US011377677B2

(12) United States Patent
Reichelt et al.

(10) Patent No.: US 11,377,677 B2
(45) Date of Patent: Jul. 5, 2022

(54) FERMENTATION PROCESS

(71) Applicant: LONZA LTD, Visp (CH)

(72) Inventors: Wieland Reichelt, Vienna (AT); Christoph Herwig, Vienna (AT); Julian Kager, Vienna (AT); Patrick Sagmeister, Vienna (AT); Matthias Funke, Naters (CH)

(73) Assignee: LONZA LTD, Visp (CH)

( * ) Notice: Subject to any disclaimer, the term of this patent is extended or adjusted under 35 U.S.C. 154(b) by 262 days.

(21) Appl. No.: 16/081,690

(22) PCT Filed: Mar. 2, 2017

(86) PCT No.: PCT/EP2017/054877
§ 371 (c)(1),
(2) Date: Aug. 31, 2018

(87) PCT Pub. No.: WO2017/149065
PCT Pub. Date: Sep. 8, 2017

(65) Prior Publication Data
US 2019/0093142 A1 Mar. 28, 2019

(30) Foreign Application Priority Data
Mar. 2, 2016 (EP) ..................... 16158294

(51) Int. Cl.
*C12P 21/00* (2006.01)
*C12P 21/04* (2006.01)
*C12N 9/00* (2006.01)
*C12N 1/38* (2006.01)
*C12P 21/02* (2006.01)

(52) U.S. Cl.
CPC ............... *C12P 21/00* (2013.01); *C12N 1/38* (2013.01); *C12P 21/02* (2013.01)

(58) Field of Classification Search
CPC .......... C12N 15/52; C12N 15/70; C12N 1/38; C12P 21/00; C12Y 604/01002; C12Y 304/17002; A61K 2039/5256; A61K 47/6843; C07K 14/765; C07K 2317/14; C07K 14/245; C07K 16/00; C12M 43/00; C12M 45/20; Y02E 50/10; Y02E 50/17
USPC ...... 435/69.7, 8.1, 13.7, 170, 320.1, 254.23, 435/483
See application file for complete search history.

(56) References Cited

U.S. PATENT DOCUMENTS

| 5,656,491 A | 8/1997 | Reese et al. |
| 7,629,167 B2 | 12/2009 | Hodge et al. |
| 8,298,054 B2 | 10/2012 | Hodge et al. |
| 2009/0305626 A1 | 12/2009 | Hope |
| 2011/0280797 A1 | 11/2011 | Mohtadi et al. |
| 2012/0077429 A1 | 3/2012 | Wernimont et al. |
| 2013/0280797 A1 | 10/2013 | Rao et al. |
| 2016/0097074 A1 | 4/2016 | Collins et al. |

FOREIGN PATENT DOCUMENTS

| EP | 0177343 A1 | 10/1984 |
| WO | 2006061174 A2 | 6/2006 |
| WO | 20006061173 A2 | 6/2006 |
| WO | 2011018376 A1 | 2/2011 |
| WO | 2013006479 A2 | 1/2013 |
| WO | 2013050551 A1 | 4/2013 |
| WO | 2014067926 A1 | 5/2014 |
| WO | 2014139608 A1 | 9/2014 |
| WO | 2015/124717 A1 | 8/2015 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
FRAME Kelly K et al., Biotechnology and Bioengineering 1990, 36, 191-197.
Kovanovsky V. et al., 2016, Bioengineering, vol. 3, No. 5, pp. 1-29.
Butler, M., "Animal cell cultures: recent achievements and perspectives in the production of biopharmaceuticals," Applied Microbiology and Biotechnology 2005. 68(3): p. 283-291.
Dabros, M. et al., "Cole-Cole, linear and multivariate modeling of capacitance data for on-line monitoring of biomass," Bioprocess and Biosystems Engineering 2009. 32(2): p. 161-173.
Dabros M et al., "Simple control of specific growth rate in biotechnological fed-batch processes based on enhanced online measurements of biomass," Bioprocess and Biosystems Engineering 2010. 33(9): p. 1109-1118.
De Assis et al., "Soft sensors development for on-line bioreactor state estimation," Computers and Chemical Engineering 2000. 24(2-7): p. 1099-1103.
Dietzsch et al., "A dynamic method based on the specific substrate uptake rate to set up a feeding strategy for Pichia pastoris," Microbial Cell Factories 2011. 10(1): p. 14.
Gnoth et al., "Control of cultivation processes for recombinant protein production: a review," Bioprocess Biosystems Engineering 2008. 31: p. 21-39.
Gnoth et al., "Product formation kinetics in genetically modified *E. coli* bacteria: inclusion body formation," Bioprocess Biosystems Engineering 2008. 31(1): p. 41-46.

(Continued)

*Primary Examiner* — Robert B Mondesi
*Assistant Examiner* — Mohammad Y Meah
(74) *Attorney, Agent, or Firm* — Medler, Ferro, Woodhouse & Mills PLLC

(57) ABSTRACT

A method for producing a recombinant protein of interest (POI) is provided, comprising the steps of (a) culturing cells in a cell culture medium to express said POI by adding a feed comprising at least one substrate to said cell culture, (b) applying a feeding strategy based on calculating, setting and optionally controlling the specific substrate uptake rate $q_s$ of the cells during the induction phase and/or production phase of the POI, wherein $q_s$ is set to be close to the maintenance rate of the cell culture; and (c) isolating said POI from the cell culture.

18 Claims, 10 Drawing Sheets

(56) References Cited

OTHER PUBLICATIONS

Jenzsch et al., "Estimation of biomass concentrations in fermentation processes for recombinant protein production," Bioprocess Biosystems Engineering 2006. 29(1): p. 19-27.
Jenzsch et al., "Generic model control of the specific growth rate in recombinant *Escherichia coli* cultivations," Journal of Biotechnology 2006. 122(4): p. 483-493.
Jenzsch et al., "Open-loop control of the biomass concentration within the growth phase of recombinant protein production processes," Journal of Biotechnology 2006. 127(1): p. 84-94.
Jobé et al., "Generally Applicable Fed-Batch Culture Concept Based on the Detection of Metabolic State by On-Line Balancing," Biotechnology and Bioengineering 2003. 82(6): p. 627-639.
Jourdier et al., "Simple Kinetic Model of Cellulase Production by Trichoderma Reesei for Productivity or Yield Maximization," Chemical Engineering Transactions 2012. 27: p. 313-318.
Passarinha et al., "Application of a Fed-Batch Bioprocess for the Heterologous Production of hSCOMT in *Escherichia coli*," Journal of Microbiology and Biotechnology 2009. 19(9): p. 972-981.
Posch A. E. et al., "Physiological Description of Multivariate Interdependencies Between Process Paramaters, Morphology and Physiology During Fed-Batch Penicillin Production," Biotechnology Progress 2014. 30(3): p. 689-699.
Ramírez O. T. et al., "Exponentially fed-batch cultures as an alternative to chemostats: The case of penicillin acylase production by recombinant *E. coli*," Enzyme Microb. Technol. 1994. 16: p. 895-903.
Risenberg et al., "High cell density cultivation of *Escherichia coli* at controlled specific growth rate," Journal of Biotechnology 1991. 20(1) p. 17-28.
Sagmeister et al., "Soft sensor assisted dynamic bioprocess control: Efficient tools for bioprocess development," Chemical Engineering Science 2013. 96: p. 190-198.

Schaepe et a., "Avoiding overfeeding in high cell density fed-batch cultures of *E. coli* during the production of heterologous proteins," Journal of Biotechnology 2014. 192 Part A: p. 146-153.
Wechselberger et al., "Efficient feeding profile optimization for recombinant protein production using physiological information," Bioprocess Biosystems Engineering 2012. 35(9): p. 1637-1649.
Wechselberger et al., "Real-time estimation of biomass and specific growth rate in physiologically variable recombinant fed-batch processes," Bioprocess Biosystems Engineering 2013. 36(9): p. 1205-1218.
Wilms et al., "High-Cell-Density Fermentation for Production of L-N-Carbamoylase Using an Expression System Based on the *Escherichia coli* rhaBAD Promoter," Biotechnology and Bioengineering 2001. 73(2): p. 95-103.
Yang et al., "Achievement of High Cell Density and High Antibody Productivity by a Controlled-Fed Perfusion Bioreactor Process," Biotechnology and Bioengineering 2001. 69(1): p. 74-82.
Cunha et al., "Methanol Induction Optimization for scFv antibody fragment production in Pichia pastoris". Biotechnology and bioengineering (2004) vol. 86:458-467.
Khatri et al., "Impact of methanol concentration on secreted protein production in oxygen-limited cultures of recombinant Pichia pastoris". Biotechnology and bioengineering (2006) vol. 93,5 : 871-9.
Khatri et al., "Oxygen-limited control of methanol uptake for improved production of a single-chain antibody fragment with recombinant Pichia pastoris". Applied Microbiology and Biotechnology (2006) vol. 72:492-498.
Capone et al., "Development of a mixed feed strategy for a recombinant Pichia pastoris strain producing with a de-repression promoter," Microb Cell Fact. 14(101):1-10.
Levisauskas et al., Bioprocess Biosyst Eng, 2003, vol. 25, No. 4, pp. 255-262.
Min et al., Progress of Bioengineering, 2000, vol. 20, No. 2, pp. 26-31.

* cited by examiner

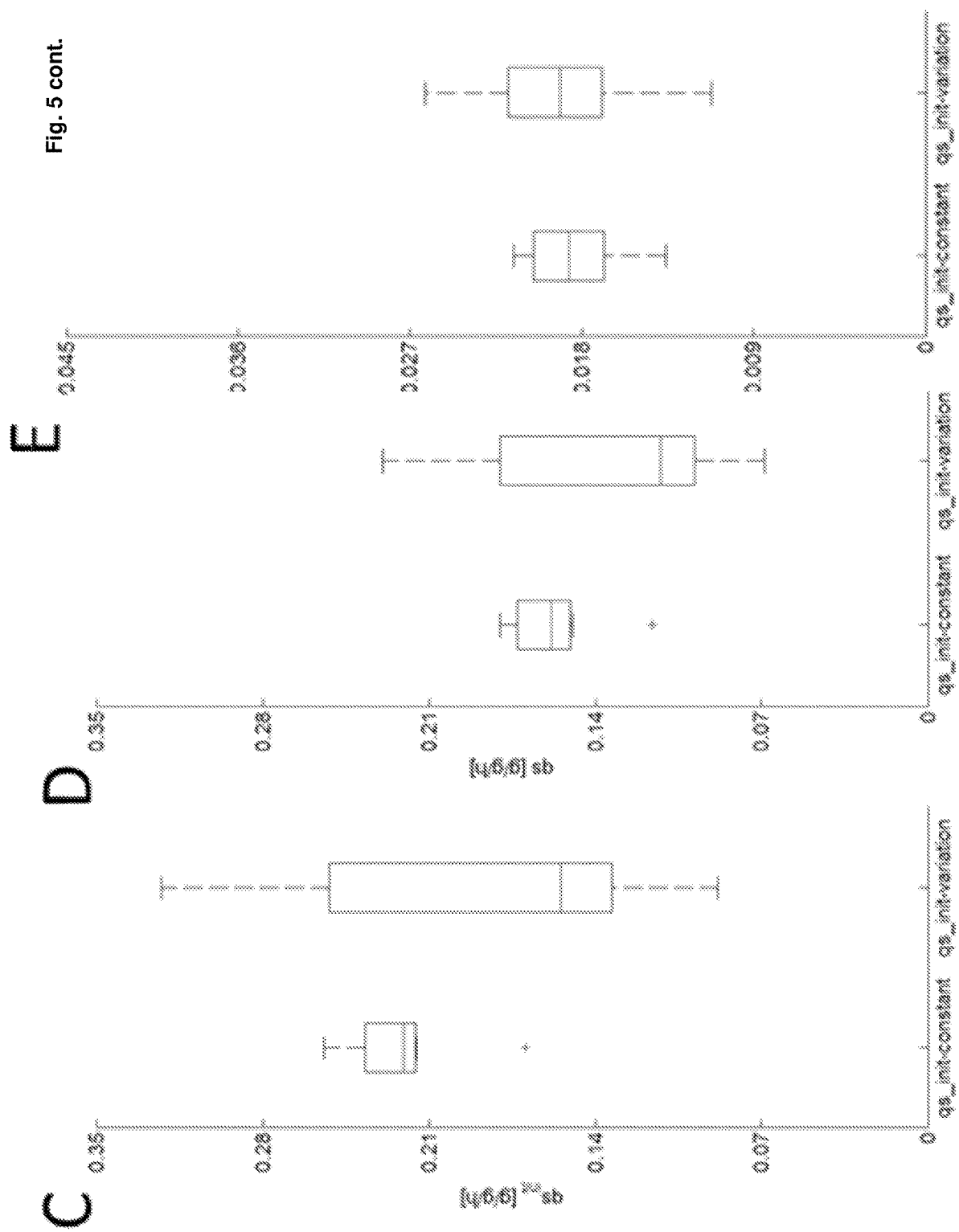

F

G

FERMENTATION PROCESS

FIELD OF THE INVENTION

The present invention relates to a fermentation method for producing high yields of recombinant protein using a novel feeding strategy.

BACKGROUND ART

Biotechnology and bioengineering play an increasing role in the modern industry and health sectors. Many of the new important active pharmaceutical ingredients are recombinant therapeutic proteins. They are formed in genetically modified microorganisms within well controlled biotechnological processes.

Bioprocess development aims at the identification and understanding of interactions between process parameters and product quality and quantity. Since bioprocess developing time is limited and the multivariate investigation of a bioprocess is a time, cost and labor intensive task, strategies are required to accelerate process development and reduce time-to market latency of biotechnological products.

Besides technological parameters such as pH-value and temperature, the supply of nutrients is the main parameter that impacting the physiology of the cell.

This feeding strategy throughout induction phase can be (a) technologically controlled e.g. a pre-defined feed profile: volumetric constant or volumetric changing. Although the feeding rate as process parameter is technologically controlled to a constant level, physiology remains uncontrolled. In such systems without any feedback control, no response is possible to changing physiological status of the cell culture, i.e. as a consequence of inducing the recombinant protein production. (b) Alternatively the feeding strategy can be physiologically controlled, which implies a quantification of the physiological status of the cells of interest.

In contrast to technological, physiological control commonly accounts for the physiological state and/or correlated changes either based on historic or literature data as fixed yield models. Alternatively real time measurements e.g. the dissolved oxygen concentration, permittivity, optical density, off-gas concentration are used to adapt the feeding strategy in response physiology.

More specifically physiological feeding strategies account for the amount of biomass in the reactor. Consequently physiological feeding strategies rely on estimating the biomass in the reactor at a single fixed time point or timely resolved throughout the induction phase. This biomass estimation is the base for calculating and controlling technically not directly assessable physiological cell culture variables. Up to now, these feeding strategies mainly focus on the specific cell growth rate µ (Gnoth et al., 2008a, Ramirez et al. 1994). Very seldom, the biomass-specific substrate uptake rate $q_S$ is controlled (Sagmeister et al., 2013). Irrespective of the targeted physiological variable the interrelation of productivity or maximum specific titer and the C-source supply throughout induction phase is of great interest.

Ramirez et al. (1994) showed a typical Luedeking-Piret kinetics of penicillin acylase production by recombinant *E. coli*, with a positive correlation of $q_P$ with µ as well as with $q_S$. In average over the respective experiment µ and $q_S$ are interrelated in this case by a constant yield coefficient $Y_{X/S}$ of 0.56 g/g. This indicates, that in this particular recombinant protein expression system the average $q_S$ does not impact the average biomass yield. In conclusion, in this case a higher µ as well as a higher $q_S$ resulted in higher $q_P$.

The possibility of influencing $q_P$ by controlling $q_S$, has been described for the organism *Pichia pastoris* by Dietzsch et al. (2011). Also this work has shown a positive effect of high $q_S$-values on the recombinant protein production. Dietzsch et al. further showed that besides the level of $q_S$, the trajectory of $q_S$ over time had a significant impact on productivity. A positive influence of a stepwise increasing feed pattern was also reported. Here the biomass measurement was performed by laborious offline sampling.

Wechselberger et al. (2012) describes the positive influence of high $q_S$-values on the productivity of a recombinant protein in *E. coli*. Wechselberger et al. also showed that the influence of a volumetric constant feeding profile can be fully explained by the influence of $q_{S_{init}}$. Hereby the volumetric constant feeding rate is calculated at the point of induction based on the biomass-specific substrate uptake rate qs in [g/g/h]. The data analysis by scaling the volumetric constant feeding rate initially to a predefined $q_S$-value showed a clear proportional correlation between $q_S$ and specific product activity.

WO2013/006479 discloses a method for culturing mammalian cells with greater control over cell growth in order to achieve high product titer cell cultures. Cell growth arrest is induced in the production phase by perfusion with a serum-free perfusion medium having a defined L-asparagine concentration. Samples were taken daily for assessing the culture. A controlled-fed perfusion process which results in enhanced monoclonal antibody productivity is described by Yang J D et al. Controlled feeding is achieved by replenish depleted constituents while maintaining the key metabolite-producing nutrients at low levels to minimize the formation of toxic metabolites (Yang J D et al., Biotechnology and Bioengineering 2000, 69(1):74-82). Jourdier E. et al. describe a simple kinetic model of cellulase production by *Trichoderma reesei* on lactose. The model allows simulating and comparing different cultivation strategies under industrial constraints (Jourdier E. et al., Chemical Engineering Transactions 2012:313-318). Achievements and perspectives in the production of biopharmaceuticals in different animal cell cultures, such as Chinese hamster ovary (CHO), mouse myeloma (NSO), baby master kidney (BHK), human embryonic kidney (HEK-293) or human-retina-derived (PER-C6) cells is described by Butler M (Butler M., Applied Microbiology and Biotechnology 2005, 68(3):283-291.

As the cited examples show, in literature mainly information is found about the positive interrelation of the maximum specific activities and the nutrient feeding to the culture. This is true for every feed control, either by µ-control or by $q_S$-control.

It is desirable to provide an improved method for highly efficient bioprocesses yielding maximum amounts of active protein. Therefore, it is the object of the present invention to provide for an improved method for fermentation products using a surprisingly negative correlation of maximum specific titers and substrate availability.

SUMMARY OF INVENTION

The objective is addressed by the subject matter as claimed.

According to the invention there is provided a method for producing a recombinant protein of interest (POI) comprising: (a) culturing cells in a cell culture medium to express said POI by adding a feed comprising at least one substrate to said cell culture, (b) applying a feeding strategy based on calculating, setting and optionally controlling the specific substrate uptake rate $q_S$ of the cells during the induction phase and/or production phase of the POI, wherein $q_S$ is set to be close to the maintenance rate of the cell culture; and (c) isolating said POI from the cell culture.

According to a specific embodiment the specific substrate uptake rate $q_S$ is set to be in the range of about the maintenance rate of the cell culture e.g. 0.03 to 0.15 g/g/h, preferably of 0.05 to 0.12 g/g/h, more preferably of 0.08 to 0.12 g/g/h, most preferably $q_S$ is about 0.12 g/g/h.

According to a specific embodiment the specific substrate uptake rate $q_S$ is controlled or uncontrolled after being set to the determined value.

According to a specific embodiment the specific substrate uptake rate $q_S$ is controlled at on a constant value (+/−15%) during at least 50% time of the production phase of said protein of interest, wherein $q_S$ is 0.03 g/g/h, 0.04 g/g/h, 0.05 g/g/h, 0.06 g/g/h, 0.07 g/g/h, 0.08 g/g/h, 0.09 g/g/h, 0.1 g/g/h, 0.11 g/g/h, 0.12 g/g/h, 0.13 g/g/h, 0.14 g/g/h or 0.15 g/g/h, most preferably 0.12 g/g/h.

According to a specific embodiment the specific substrate uptake rate $q_S$ is set at least once by adjusting the feed rate or controlled during at least 50% time of the production phase of said protein of interest, wherein $q_S$ is within the range of 0.15 to 0.05 g/g/h, preferably decreases from 0.15 to equal to or less than 0.12 g/g/h, from 0.15 to 0.10 g/g/h, from 0.15 to 0.07 g/g/h, from 0.15 to 0.05 g/g/h, from 0.12 to 0.1 g/g/h, from 0.12 to 0.07 g/g/h, from 0.12 to 0.05 g/g/h, from 0.1 to 0.07 g/g/h, from 0.1 to 0.05 g/g/h, or from 0.1 to 0.03 g/g/h.

According to a specific embodiment the specific substrate uptake rate $q_S$ is set at least once by adjusting the feed rate or controlled during at least 50% time of the production phase of said recombinant protein within the range of 0.03 to 0.15 g/g/h, preferably increases from 0.03 to equal to or more than 0.12 g/g/h, from 0.03 to 0.10 g/g/h, from 0.03 to 0.07 g/g/h, from 0.05 to 0.15 g/g/h, preferably increases from 0.05 to equal to or more than 0.12 g/g/h, from 0.05 to 0.10 g/g/h, from 0.05 to 0.07 g/g/h, from 0.07 to 0.12 g/g/h, from 0.07 to 0.10 g/g/h, from 0.10 to 0.12 g/g/h, or from 0.10 to 0.15 g/g/h.

According to a specific embodiment, the specific substrate uptake rate $q_S$ is constant, decreasing or increasing during at least 50%, at least 75%, at least 80% or at least 95% of the production phase of said protein of interest.

According to a specific embodiment the specific substrate feeding rate $q_S$ is positive in case of substrate feeding and corresponds to the scientifically established specific substrate uptake rate $q_S$, which is conventionally negative.

According to a specific embodiment, the specific substrate uptake rate $q_S$ is controlled or set at least once by adjusting the feed rate accordingly.

According to a specific embodiment, the calculation of the specific substrate uptake rate $q_S$ is performed with the start of the induction phase/production phase. According to a specific embodiment, the biomass is determined by once or by a real time biomass estimation and or measurement.

According to a specific embodiment, real time biomass measurement is performed using a soft sensor or a hard sensor.

According to a further specific embodiment the at least one substrate is a carbohydrate.

According to a specific embodiment the carbohydrate is a hexose such as glucose, fructose, galactose, rhamnose or mannose, a disaccharide, such as saccharose, an alcohol, such as glycerol or ethanol, or a mixture thereof.

According to a specific embodiment, the substrate is glucose or glycerol (gly).

Specifically, the feed is chemically defined.

The feed may be added to the culture medium in the liquid form or else in an alternative form, such as a solid, e.g. as a tablet or other sustained release means, or a gas, e.g. carbon dioxide.

According to a specific embodiment the cells are selected from the group consisting of a eukaryotic cell or prokaryotic cell.

According to a specific embodiment, the eukaryotic cell is selected from the group consisting of mammalian, insect, yeast, filamentous fungi, and plant cell, preferably a yeast cell, most preferably *Pichia pastoris*, *Komagataella pastoris*, *K. phaffii*, or *K. pseudopastoris*.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EBI, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBvl3.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris*, *Pichia methanolica*, *Pichia kluyveri*, and *Pichia angusta*), *Komagataella* genus (e.g. *Komagataella*

*pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii,*), the *Geotrichum* genus (e.g. *Geotrichum fermentans*), *Hansenula polymorpha, Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus*. *Bacillus* that can be used is, e.g. the *B. subtilis, B. amyloliquefaciens, B. licheniformis, B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12th Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

According to a specific embodiment, the prokaryotic cell is selected from the group consisting of *E. coli, B. subtilis*, and *Pseudomonas*.

According to a specifically preferred embodiment, the prokaryotic cell is *E. coli*.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce peptides or proteins of interest (POI) e.g., antibodies, e.g., monoclonal antibodies, and/or recombinant proteins, for therapeutic use. In embodiments, the cultured cells produce amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

According to a specific embodiment the majority of the recombinant protein is located in the cytoplasm, the periplasm or extracellularly, preferably in the periplasm.

According to a specific embodiment, the protein of interest (POI) is a recombinant protein.

Specifically, the POI is a eukaryotic protein, preferably a mammalian protein.

A POI produced according to the invention may be a multimeric protein, preferably a dimer or tetramer.

According to one aspect of the invention, the POI is a recombinant or heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a recombinant protein.

A specific protein of interest is an antigen binding molecule such as an antibody, or a fragment thereof. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH or VHH or V-NAR.

According to a specifically preferred embodiment, the recombinant protein is an immunoglobulin, preferably an antibody or antibody fragment, most preferably a Fab or scFv antibody.

In further embodiments, the protein of interest (POI) is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphanate, octocog alpha, Factor VIII, palifermin, indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (subcutaneous implant, Hydron), deslorelin, histrelin, nafarelin, leuprolide sustained release depot (ATRI-GEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant Cl esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexiganaacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alphagalactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-0S1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, or TP-9201.

In some embodiments, the POI is adalimumab (HUMIRA), infliximab (REMICADE™), rituximab (RITUXAN™/MAB THERA™), etanercept (ENBREL™) bevacizumab (AVASTINT™), trastuzumab (HERCEPTIN™), pegrilgrastim (NEULASTA™), or any other suitable POI including biosimilars and biobetters.

Other suitable POIs are those listed below in Table 1 and in US2016/0097074.

TABLE 1

| Reference Listed Drug | Protein Product (POI) |
| --- | --- |
| Actimmune ® | interferon gamma-1b |
| Activase ®/Cathflo ® | alteplase; tissue plasminogen activator |
| Advate | recombinant antihemophilic factor |
| Albutein ® | human albumin |
| Aldurazyme ® | laronidase |
| Alferon N ® | interferon alfa-N3, human leukocyte derived |
| Alphanate ® | human antihemophilic factor |
| AlphaNine ® SD | virus-filtered human coagulation factor IX |
| Amevive ® | alefacept; recombinant, dimeric fusion protein LFA3-Ig |
| Angiomax ® | bivalirudin |
| Aranesp ™ | darbepoetin alfa |
| Avastin ™ | bevacizumab |
| Avonex ® | interferon beta-1a; recombinant |
| BeneFix ™ | coagulation factor IX |
| Betaseron ® | enterferon beta-1b |
| BEXXAR ® | tositumomab |
| Bioclate ™ | antihemophilic factor |
| BioTropin ™ | human growth hormone |
| BOTOX ® | botulinum toxin type A |
| Campath ® | alemtuzumab |
| CEA-Scan ® | acritumomab; technetium-99 labeled |
| Ceredase ® | alglucerase; modified form of beta-glucocerebrosidase |
| Cerezyme ® | imiglucerase; recombinant form of beta-glucocerebrosidase |
| CroFab ™ | crotalidae polyvalent immune Fab, ovine |
| DigiFab ™ | digoxin immune fab [ovine] |
| Elitek ® | rasburicase |
| ENBREL ® | etanercept |
| Epogen ® | epoietin alfa |
| Erbitux ™ | cetuximab |
| Fabrazyme ® | algasidase beta |
| Fertinex ™ | urofollitropin |
| Follistim ™ | follitropin beta |
| FORTEO ® | teriparatide |
| GenoTropin ® | human somatropin |
| GlucaGen ® | glucagon |
| Gonal-F ® | follitropin alfa |
| Helixate ® | antihemophilic factor |
| HEMOFIL | antihemophilic factor; factor XIII |
| Hepsera ™ | adefovir dipivoxil |
| Herceptin ® | trastuzumab |
| Humalog ® | insulin |
| Humate-P ® | antihemophilic factor/von Willebrand factor complex-human |
| Humatrope ® | somatotropin |
| HUMIRA ™ | adalimumab |
| Humulin ® | human insulin |
| Hylenex ™ | recombinant human hyaluronidase |
| Infergen ® | interferon alfacon-1 |
| Integrilin ™ | eptifibatide |
| Intron A ® | alpha-interferon |
| Kepivance | palifermin |

TABLE 1-continued

| Reference Listed Drug | Protein Product (POI) |
| --- | --- |
| Kineret ™ | anakinra |
| Kogenate ® FS | antihemophilic factor |
| Lantus ® | insulin glargine |
| Leukine ®/Leukine ® | granulocyte macrophage |
| Liquid | colony-stimulating factor |
| Luveris | lutropin alfa for injection |
| LYMErix ™ | OspA lipoprotein |
| LUCENTIS ® | ranibizumab |
| Mylotarg ™ | gemtuzumab ozogamicin |
| Naglazyme ™ | galsulfase |
| Natrecor ® | nesiritide |
| Neulasta ™ | pegfilgrastim |
| Neumega ® | oprelvekin |
| Neupogen ® | filgrastim |
| NeutroSpec ™ (formerly LeuTech ®) | fanolesomab |
| Norditropin ®/Norditropin Nordiflex ® | somatropin |
| Novantrone ® | mitoxantrone |
| Novolin L ® | insulin; zinc suspension; |
| Novolin N ® | insulin; isophane suspension |
| Novolin R ® | insulin, regular; |
| Novolin ® | insulin |
| NovoSeven ® | coagulation factor VIIa |
| Nutropin ® | somatropin |
| Octagam ® | human immunoglobulin intravenous |
| Oncaspar ® | PEG-L-asparaginase |
| Orencia ™ | abatacept, fully human soluble fusion protein |
| Orthoclone OKT3 ® | muromomab-CD3 |
| Orthovisc ® | high-molecular weight hyaluronan |
| Ovidrel ® | human chorionic gonadotropin |
| Pacis ® | live attenuated Bacillus Calmette-Guerin |
| Pegasys ® | peginterferon alfa-2a |
| PEG-Intron ™ | pegylated version of interferon alfa-2b |
| Plenaxis ™ | abarelix (injectable suspension); gonadotropin-releasing hormone antagonist |
| Procrit ® | epoietin alfa |
| Proleukin, IL-2 ® | aldesleukin |
| Protropin ® | somatrem |
| Pulmozyme ® | dornase alfa |
| RAPTIVA ™ | efalizumab; selective, reversible T-cell blocker |
| Rebetron ™ | combination of ribavirin and alpha interferon |
| Rebif ® | interferon beta 1a |
| Recombinate ® rAHF/ | antihemophilic factor |
| ReFacto ® | antihemophilic factor |
| Refludan ® | lepirudin |
| REMICADE ® | infliximab |
| ReoPro ™ | abciximab |
| Retavase ™ | reteplase |
| Rituxan ™ | rituxima |
| Roferon-A ® | interferon alfa-2$^a$ |
| Saizen ® | somatropin |
| SecreFlo ™ | synthetic porcine secretin |
| Simulect ® | basiliximab |
| SOLIRIS (R) | eculizumab |
| SOMAVERT ® | pegvisomant |
| Synagis ™ | palivizumab; |
| Thyrogen ® | thyrotropin alfa |
| TNKase ™ | tenecteplase |
| TYSABRI ® | natalizumab |
| Venoglobulin-S ® | human immune globulin intravenous 5% and 10% solutions |
| Wellferon ® | interferon alfa-n1, lymphoblastoid |
| Xigris ™ | drotrecogin alfa |
| Xolair ® | omalizumab; recombinant Antibody targeting immunoglobulin-E |
| Zenapax ® | daclizumab |
| Zevalin ™ | ibritumomab tiuxetan |
| Zorbtive ™ (Serostim ®) | somatotropin |

In some embodiments, the POI is a hormone, a blood clotting/coagulation factor, a cytokine/growth factor, an antibody molecule, a fusion protein, a protein vaccine, or a peptide as shown in Table 2.

TABLE 2

Exemplary POI

| Therapeutic Product type | Product (POI) | Trade Name |
|---|---|---|
| Hormone | Erythropoietin, Epoetin alpha | Epogen, Procrit |
| | Darbepoetin | Aranesp |
| | Growth hormone (GH) Somatotropin | Genotropin, Humatrope, Norditropin, NovlVitropin, Nutropin, Omnitrope, Protropin, Saizen, Serostim, Valtropin |
| | Human follicle-stimulating hormone (FSH) | Gonal-F, Follistim |
| | Human chorionic gonadotropin | Ovidrel |
| | Lutropin alpha | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/ Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/ Growth factor | Type I alpha-interferon | Infergen |
| | Interferon-alpha-n3 (IFNαn3) | Alferon N |
| | Interferon-beta-1a (rIFN-β1α) | Avonex, Rebif |
| | Interferon-beta-1b (rIFN-β1β) | Betaseron |
| | Interferon-gamma-1b (IFNγ1β) | Actimmune |
| | Aldesleukin (interleukin 2(IL2)) | Proleukin |
| | Epidermal thymocyte activating factor; ETAF | |
| | Palifermin (keratinocyte growth factor; KGF) | Kepivance |
| | Becaplemin (platelet-derived growth factor; PDGF) | Regranex |
| | Anakinra (recombinant IL1 antagonist) | Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/ Protein vaccines/ Peptides | Insulin | Humulin, Novolin |
| | Hepatitis B surface antigen (HBsAg) | Engerix, Recombivax HB |
| | HPV vaccine | Gardasil |
| | Lyme Disease Vaccine (OspA) | LYMErix |
| | Anti-Rhesus(Rh) immunoglobulin G | Rhophylac |
| | Enfuvirtide | Fuzeon |
| | Spider silk, e.g., fibrion | QMONOS |

In some embodiments, the POI is a multispecific protein, e.g., a bispecific antibody as shown in Table 3.

TABLE 3

Bispecific formats of a POI

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adeno-carcinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |

TABLE 3-continued

Bispecific formats of a POI

| Name (other names, sponsoring organizations) | BsAb format | Targets | Proposed mechanisms of action | Development stages | Diseases (or healthy volunteers) |
|---|---|---|---|---|---|
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharma-ceuticals) | HSA body | HER2, HER3 | Blockade of 2 receptors | Phase II Phase I | Gastric and esophageal cancers Breast cancer |
| MM-141, (Merrimack Pharma-ceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/ VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |

TABLE 3-continued

Bispecific formats of a POI

| Name (other names, sponsoring organizations) | BsAb format | Targets | Proposed mechanisms of action | Development stages | Diseases (or healthy volunteers) |
|---|---|---|---|---|---|
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ ACE910 (Chugai, Roche) | ART-Ig | Factor IXa, factor X | Plasma coagulation | Phase II | Hemophilia |

The devices, facilities and methods described herein are suitable for use in and with culturing any desired cell line including prokaryotic and/or eukaryotic cell lines. Further, in embodiments, the devices, facilities and methods are suitable for culturing any cell type including suspension cells or anchorage-dependent (adherent) cells and are suitable for production operations configured for production of pharmaceutical and biopharmaceutical products—such as polypeptide products (protein of interest (POI)), nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, POIs such as exemplified herein including antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), or viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., POIs including proteins, peptides, or antibiotics, amino acids, nucleic acids (such as DNA or RNA), synthesized by said cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, micro-fiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor". For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

BRIEF DESCRIPTION OF DRAWINGS

FIG. 5A shows the correlation of initial substrate uptake rate and maximum specific titers;

FIG. 5B shows the correlation of mean substrate uptake rate and maximum specific titers;

FIGS. 5C-5E: Comparison of observed and induced variance within the conducted experiments (n=12) qs_init-constant labels the group of experiments conducted with a constant $q_{S_{init}}$; qs_init variation labels the group of experiments conducted to investigate the impact of different volumetric constant feeding regimes;

FIG. 5C shows the induced variance in $qs_{init}$ [g/g/h];

FIG. 5D shows the calculated variance in $q_S$ [g/g/h];

FIG. 5F: Statistical analysis of the effect of the mean specific substrate uptake rate on maximum specific titers.

FIG. 5G: Statistical analysis of the effect of the initial specific substrate uptake (Equation 3) rate on maximum specific titers.

DETAILED DESCRIPTION OF THE INVENTION

Figure 1A:
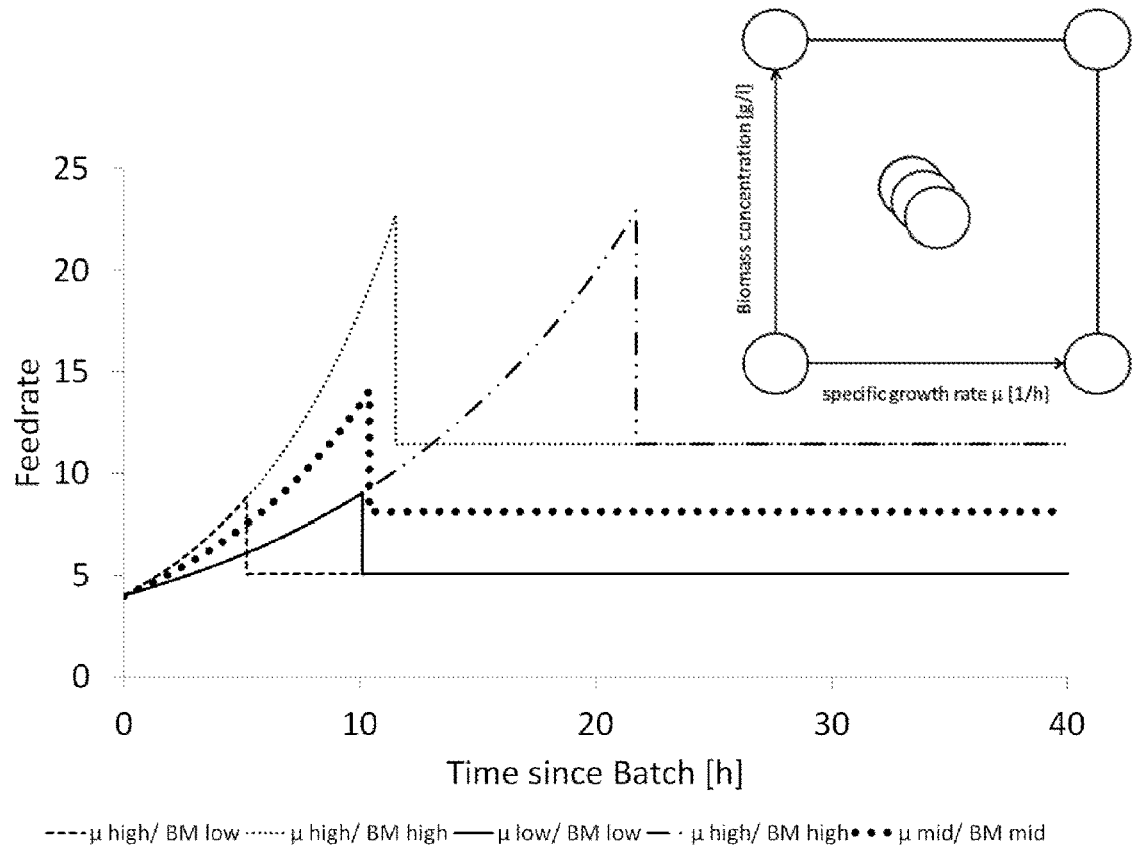
FIG. 1A: Exemplary feeding profile with different pre-induction specific growth rates and different biomass concentrations at point of induction.

Methods for improved production of a protein of interest by culturing cells are provided, wherein the feeding strategy is based on the specific substrate uptake. The methods involve calculating, setting and optionally controlling the specific substrate uptake rate $q_S$.

Considering physiology in terms of a physiological feeding strategy manufacturing of recombinant products is improved. Hereby the feeding strategy is calculated based on an at least one time or timely resolved biomass estimation. This approach facilitates the improvement of specific activity of the one or more proteins of interest and/or the increase of productivity of the one or more proteins of interest.

Surprisingly this method leads to increased specific activities and/or yield or titer of the one or more proteins of interest especially if substrate availability is low.

Specific terms as used throughout the specification have the following meaning.

The term "culturing" a cell refers to contacting a cell with a cell culture medium under conditions suitable to the survival and/or growth and/or proliferation of the cell.

The terms "culture" and "cell culture" as used herein refer to a cell population that is suspended in a cell culture medium under conditions suitable to survival and/or growth of the cell population. As used herein, these terms may refer to the combination comprising the cell population (e.g., the host cell culture) and the medium in which the population is suspended.

The term "cell culture medium" as used herein shall mean a nutritive solution for the maintenance, growth, propagation, or expansion of cells. Cell culture medium may be optimized for a specific cell culture use, including, for example, cell culture growth medium which is formulated to promote cellular growth or cell culture production medium which is formulated to promote recombinant protein production. The terms nutrient, ingredient, and component are used interchangeably herein to refer to the constituents that make up a cell culture medium.

The term "chemically defined" with respect to cell culture medium, such as a feed medium in a fed-batch process, shall mean a growth medium suitable for the in vitro cell culture of a production cell line, in which all of the chemical components and peptides are known. Typically a chemically defined medium is entirely free of animal-derived components and represents a pure and consistent cell culture environment.

The term "feed" or "feed medium" as used herein shall mean: The feed or feed medium comprises a substrate or carbon source, it may be chemically defined or a complex medium or a mixture thereof. The feed or feed medium may comprise an inductor or inducer regulating a control sequence such as a promoter.

The term "inductor" or "inducer" as used herein shall mean the substance which is capable to induce expression of a POI. The inductor or inducer may be added to the cell culture as part of the feed or separately. In case of depletion induced expression systems the lack of such inductor or "inducer" triggers expression of a POI.

The term "induction" as used herein shall mean the point during a respective bioprocess at which the metabolism is altered to favor expression of the POI by supplementing an inducer or by depletion some sort of chemical compound.

The term "induction phase" as used herein shall mean the time period of a cell culture after pre-induction and induction during which the cells are producing a recombinant protein or POI.

As used herein, the "production phase" of a cell culture refers to the period of time during which cell growth has plateaued or is maintained at a near constant level. During the production phase, logarithmic cell growth has ended and production of a POI is primary. During this period of time the medium is generally supplemented to support continued protein production and to achieve the desired POI.

The term "host" or "cell" or "cell line" as used herein refers to an established clone of a particular cell type that has acquired the ability to proliferate over a prolonged period of time. The term "host cell line" refers to a cell line as used for expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process, such as a POI. The term "eukaryotic host" or "eukaryotic cell" or "eukaryotic cell line" shall mean any eukaryotic cell or organism, the term "prokaryotic host" or "prokaryotic cell" or "prokaryotic cell line" shall mean any prokaryotic cell or organism, each of which may be cultivated to produce a protein of interest (POI) or a host cell metabolite. It is well understood that the term does not include human beings.

The term "expression" or "expression system" or "expression cassette" refers to nucleic acid molecules comprising or containing a desired coding sequence encoding a POI and control sequences in operable linkage, so that hosts transformed or transfected with these sequences are capable of producing the encoded protein such as the POI or host cell metabolites. Preferably, the cells comprising a nucleic acid encoding a recombinant protein of interest (POI). Preferably, the control sequence is a promoter. Preferably, the promoter is a regulable promoter such as an inducible promoter. Preferably, the regulable or inducible promoter is selected from the group consisting of sugar inducible promoter or depletion inducible promoter. A sugar inducible promoter may be a rhamnose promoter (rhaBAD, WO2006061174A2), a melibiose promoter (WO2006061173A2), an arabinose promoter, lac promoter, or mannose promoter (WO2011018376A1). A depletion inducible promoter may for example be a phosphate depletion inducible promoter such a phoA (EP0177343) or a carbon source depletion inducible promoter such as pG1, pG3, pG4, pG6, pG7, or pG8 (WO2013050551A1). Alternatively, the promoter may be a constitutive promoter such as pCS1 (WO2014139608A1), an AOX promoter, a T5 promoter, T7 promoter, or an IPTG inducible promoter. The expression system or expression cassette may further comprise a signal sequence or secretion sequence encoding a signal peptide to allow release or secretion of the POI. Preferred signal sequences are in case of *E. coli* ompA, pelB, lamB, malE, phoA, bla, OppA, TreA, MppA, or BglX, or in case of *Pichia* or *Komagataella* alpha mating factor or EPX-L (WO2014067926). In order to effect transformation, the expression system may be included in a vector; however, the relevant DNA may also be integrated into the host chromosome. Expression may refer to secreted or non-secreted expression products, including polypeptides or metabolites.

According to a further specific embodiment, the promoter and/or signal sequence is not natively associated with the gene encoding the recombinant protein or POI, wherein the recombinant protein or POI is a heterologous protein, preferably selected from therapeutic proteins, including immunoglobulins such as antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI.

Specifically, the recombinant protein or POI is a eukaryotic protein, preferably a mammalian protein. A recombinant protein or POI produced according to the invention may be a multimeric protein, preferably a dimer or tetramer. According to one aspect of the invention, the recombinant protein or POI is a heterologous protein, preferably selected from therapeutic proteins, including immunoglobulins such as antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a recombinant protein. A specific recombinant protein or POI is an antigen binding molecule such as an antibody, or a fragment thereof. Among specific recombinant proteins or POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or mini-bodies and single-domain antibodies like VH or VHH or V-NAR.

The term "pre-induction phase" as used herein shall mean the time period prior of cell culturing prior to the induction phase i.e. prior to the addition of an inducer or inductor.

The term "substrate" or "carbon source" as used herein shall mean a metabolizable carbon substrate, typically a carbohydrate, suitable as a carbon source for microorganisms. The substrate or carbon source may be any type of organic carbon suitable used for a cell culture. According to a specific embodiment the carbon source is a carbohydrate or sugar such as a hexose such as glucose, fructose, galactose or mannose, a disaccharide, such as saccharose, an alcohol, such as glycerol or ethanol, or a mixture thereof. According to a further specific embodiment, the substrate or carbon source is glucose or glycerol or a mixture thereof. The substrate or carbon source is also called primary carbon source since it is the carbon source which is preferentially metabolized over other, secondary substrates or carbon sources which are less preferred by a cell to be metabolized, i.e. used for biomass production or anabolism. The substrate or carbon source preferably metabolized is different from a carbon source (secondary carbon source) which can act as an inducer for a carbon source inducible promoter such as for example methanol to induce an AOX promoter, mannose to induce a mannose promoter, rhamnose to induce a rhamnose promoter, melibiose to induce a melibiose promoter or arabinose to induce an arabinose promoter.

The term "substrate feeding rate" as used herein shall mean the rate of a substrate such as a carbon source (c-source) fed in g/L/h or c-mol/L/h or ml/L/h, i.e. the amount of carbon source per fermentation volume and time unit. In other words, the substrate feeding rate is the amount of carbon source which is needed to maintain the metabolism of the cell. Preferably, the substrate feeding rate is continuously applied at parts or during the entire fed-batch phase.

The term "feeding strategy" as used herein shall mean the method of defined supply of substrate to the microorganisms in the bioreactor throughout induction phase The term "calculating" as used herein shall mean the evaluation of the substrate uptake rate at a distinct time point, which is typically performed by applying offline biomass measurements.

The term "setting" as used herein shall mean the adjustment of the substrate feeding rate set point or profile based on $q_S$ according to the at least one time biomass estimation.

The term "at least" as used herein refers to a situation wherein a particular value is the same as said particular value or more. For example, "at least 1" is understood to be the same as "1 or more" i.e., 1, 2, 3, 4, 5, 6, 7, 8, 9, 10, 11, 12, 13, 14, 15, . . . , etc.

The term "controlling" as used herein shall mean a regular, reoccurring calculation of the substrate uptake rate and subsequent (re)adjustment of the feed rate. This is typically done by real time estimation/measurement of the biomass which facilitates the calculation of the specific substrate uptake rate and a subsequently the automated feed rate adjustment.

The term "biomass estimation" as used herein shall refer to a quantification of biomass based on an online or offline determination or estimation of the biomass content in the bioreactor.

The term "maintenance rate" of the cell or "cell maintenance rate" as used herein shall mean the cells' energy requirements for housekeeping/upkeep of physiologic functions which include for example maintaining concentration gradients over the cell membrane, DNA repair or RNA synthesis. At maintenance rate no or almost no or even a slight decrease in net biomass synthesis is yielded, and the specific growth rate µ is about zero (0) or below 0. The term "close to the maintenance rate" as used herein shall include the maintenance rate as defined above and also values of about 50%, 45%, 40%, 35%, 30%, 25%, 20%, 15%, or about 10%, or about 5%, or about 3% or about 2% above said maintenance rate. Under such conditions of slightly higher than maintenance rate cell biomass synthesis can occur and the specific growth rate µ is close to 0, or above or slightly above 0. In preferred embodiments µ at such slightly higher values than maintenance rate is in the range of 0.0001-0.0004/h, 0.0005-0.0009/h, 0.001-0.004/h, 0.005-0.009/h, 0.01-0.04/h, 0.05-0.09/h, or 0.1-0.2/h, preferably, within the range of 0.005-0.015/h, most preferably within the range of 0.008-0.0012.

The term "soft sensor" as used herein refers to process analytical devices that grant access to important non-measured process variables by mathematical processing of readily available process data. They typically come with reduced costs compared to hard type sensors and do not violate the sterility barrier of the system.

The term "hard sensor" as used herein refers to process devices for measuring important process variable such as the broth turbidity, broth fluorescence or permittivity.

The term "about", as used herein and unless specifically stated or obvious from context is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The biomass-specific substrate uptake rate $q_S$ is directly coupled to the physiological status of the cell culture and, thus, has a high impact on the biomass-specific productivity $q_P$. For controlling the parameter $q_S$ and, thus, manipulating the specific productivity $q_P$, the biomass concentration to a given time-point in the fermenter has to be known.

The term "real time biomass estimation" as used herein shall mean a real time biomass estimation performed within a running process based on estimation of the biomass Upon induction alterations in the energy metabolism, caused by protein overexpression, cause variations of the yield coefficients (Jenzsch, Simutis et al. 2006, Schaepe, Kuprijanov et al. 2014). Therefore, various approaches for real time biomass estimation have been reported (Riesenberg, Schulz et al. 1991, de Assis and Filho 2000, Jobe, Herwig et al. 2003, Jenzsch, Gnoth et al. 2006, Jenzsch, Simutis et al. 2006, Passrinha, Bonifacio et al. 2009, Dabros, Schuler et al. 2010). These real time approaches can be categorized by the underlying principle of biomass estimation: hard type sensor (Dabros, Dennewald et al. 2009) and model based (Jenzsch, Simutis et al. 2006, Jenzsch, Gnoth et al. 2006). An example for a model based approach would be using soft sensors (Wechselberger 2013). The central idea behind a soft sensor is to use relatively easily accessible on-line date for the estimation of important process variables.

The term "$q_{Sinit}$" refers to the specific substrate uptake rate which is reached at the point of induction by setting the feeding rate. The term "$q_S$", as used herein refers to the average of the timely variable specific substrate uptake rate over a process phase.

In contrast to the state-of-the-art knowledge the present invention illustrates for the first time the first surprising finding that unusual low (both, un-controlled and controlled) $q_S$-values lead to a productivity increase for recombinantly expressed proteins. The second surprising finding was that the titers of recombinant proteins can be increased up to 50% when actively controlling the physiological parameter specific substrate uptake rate $q_S$ at a constant low level during the production phase.

Moreover, hardware probes are available, which allow for the measurement of biomass online in real time, after a process and organism-specific calibration has been established. These commercially available biomass measurements are based e.g. on capacitance measurement (e.g. Aber Instruments, Hamilton) or optical density (e.g. Mettler Toledo).

As stated above, biomass measurement is the base for calculating physiological parameters biomass growth rate µ and substrate consumption rate $q_S$. Also for a transferable expression of the productivity, the biomass value is necessary:

$$\mu = 1/X * dX/dt \tag{1}$$

$$q_S = 1/X * dS/dt \tag{2}$$

$$q_P = 1/X * dP/dt \tag{3}$$

µ biomass growth rate [1/h]
X biomass concentration [g/L]
$q_S$ biomass-specific substrate uptake rate [g/g/h]
S substrate concentration [g/L]
$q_P$ biomass-specific production rate [g/g/h]
P product concentration [g/L]
t cultivation time [h]

In fed-batch fermentations, the fed substrate is immediately consumed by the cells. Therefore, the substrate uptake rate is equal to the biomass-specific substrate feed rate, and, thus deductible from the pump rate of the feed pump and the current biomass concentration. Both values, the growth rate and the substrate uptake rate, are linked by the biomass-substrate yield coefficient $Y_{X/S}$:

$$Y_{X/S} = \mu/q_S \quad (4)$$

$Y_{X/S}$ biomass-substrate yield coefficient [g/g]

From equation 4 follows that µ can directly be converted to $q_S$ and vice versa, if the yield coefficient $Y_{X/S}$ is known. This conversion is complicated if $Y_{X/S}$ is not constant. A change in the $Y_{X/S}$-value is observed during the production phase, if the recombinantly expressed protein has a significant impact on the metabolic state of the cells. This is true for a wide range of proteins, since their expression puts a metabolic burden on the cellular protein synthesis- and energy metabolism.

The physiological difference between µ and $q_S$ can be generalized by describing the microbial growth µ just as a result of the substrate uptake $q_S$ of the cell. The principal parameter (besides environmental factors), which controls the cell physiology, is the availability of nutrients. Only if nutrients are available, the cell can convert them, either for cell division, (recombinant) protein production or maintenance. This correlation can be described as shown in equation 5:

$$q_S = 1/Y_{X/S}*\mu + 1/Y_{P/S}*q_P + m*X \quad (5)$$

$Y_{P/S}$ product-substrate yield coefficient [g/g]
m maintenance coefficient [1/h]

From this point of view, a control of the upstream parameter $q_S$ is more meaningful instead of controlling the "symptom" µ.

As described in equation 4 and 5, the correlation between µ and $q_S$ is given by $\mu = Y_{X/S}*q_S$. The yield coefficient $Y_{X/S}$ is typically 0.4-0.5 g/g for a non-induced *E. coli* cell, but can significantly be reduced when POI expression is induced. For many recombinant proteins, the protein expression results in a high metabolic burden for the cells, i.e. much energy is consumed by the protein synthesis network and secondary processes such as folding or proteolysis. Moreover, the recombinant product may even be toxic to the cells and completely hinder cell growth ($Y_{X/S}$~0).

An additional drawback of a µ-control is a technical drawback. Comparing equation 1 and 2, it can be seen that the calculation of µ takes the error-prone measurement of the biomass X twice into account (compared to 1 X-value in the $q_S$-calculation). Despite this disadvantage µ-control is often used in fermentation processes such as for example as described in Gnoth et al., 2008a.

To our knowledge, in literature no report can be found that shows an increasing productivity at very low nutrient supply. Even at such low nutrient supply which only ensures cell survival at its maintenance rate or close to its maintenance rate as defined herein. Thereby it does not matter, if the feeding strategy is a simply technological e.g. pump rate, or a physiological approach by basing the feeding strategy on physiological variables as $q_S$ or even µ.

The present first time invention also applies to the real time biomass estimation with the purpose to control $q_S$ at an optimal level for high recombinant protein production. In contrast to the state-of-the-art knowledge, the performed experiments resulted in the first surprising finding that the titers of recombinant proteins, such as immunoglobulins (e.g., FAbs), can be increased up to 50% when actively controlling the physiological variable of the specific substrate uptake rate $q_S$ throughout induction phase.

To our knowledge, no one has shown so far that at such a low level of $q_S$, there is such a significant increase in the cells productivity only triggered by physiological process control. The first finding of advantageous $q_S$ control is generally independent from the actual $q_S$-level. Specifically, if the $q_S$-value is actively set, preferably, at the start of the induction phase, to the appropriate level and optionally controlled. Upon the induction phase, the specific uptake rate is actively set and optionally controlled to be in a range the cell maintenance rate, or slightly above the cell maintenance rate as defined above.

The second surprising finding is that unusual low (both, un-controlled and controlled) $q_S$-values generally lead to a productivity increase for recombinantly expressed proteins, such as antibody fragments (Fab), in cells, such as prokaryotic cells, for example *E. coli* cells.

To our knowledge, no correlation between feeding and $q_P$ has been reported, in which a very low substrate uptake rate $q_S$ has been found as the optimum for a high $q_P$. Therefore, our invention, which claims the optimal substrate feeding to be at the very low level in the range of the cell maintenance (where µ~0 and $q_S$ is ~0.03-0.15 g/g/h), is surprising and new.

Thus, surprisingly, setting and optionally also controlling the specific substrate update rate $q_S$ in the range of the cell maintenance rate or about 50%, 45%, 40%, 35%, 30%, 30%, 25%, 20%, 15%, 10% or 5% above the cell maintenance rate results in increased productivity of at least about 25%, 30%, 35%, 40%, 45%, or at least about 50% when compared to cell cultures controlled by conventional parameters such as the specific growth rate µ.

The following items further provide specific aspects of the disclosure, and specific embodiments to practice the teachings provided herein.

1. A method for producing a recombinant protein of interest (POI) comprising:
(a) culturing cells in a cell culture medium to express said POI by adding a feed comprising at least one substrate to said cell culture,
(b) applying a feeding strategy based on calculating, setting and optionally controlling the specific substrate uptake rate $q_S$ of the cells during the induction phase and/or production phase of the POI, wherein $q_S$ is set to be close to the maintenance rate of the cell culture; and
(c) isolating said POI from the cell culture.

2. The method of item 1, wherein $q_S$ is in the range of 0.03 to 0.15 g/g/h, preferably of 0.05 to 0.12 g/g/h, more preferably of 0.08 to 0.12 g/g/h, most preferably $q_S$ is about 0.12 g/g/h.

3. The method of item 1 or 2, wherein $q_S$ is controlled or uncontrolled.

4. The method of item 3, wherein $q_S$ is controlled to be constant, decreasing or increasing during at least 75%, at least during 80% or at least 95% of the production phase of said POI.

5. The method of item 3 or 4, wherein $q_S$ is controlled at on a constant value (+/−15%) during at least 50% time of the production phase of said POI.

6. The method according to item 5, wherein $q_S$ is about 0.03 g/g/h, 0.04 g/g/h, 0.05 g/g/h, 0.06 g/g/h, 0.07 g/g/h, 0.08 g/g/h, 0.09 g/g/h, 0.1 g/g/h, 0.11 g/g/h, 0.12 g/g/h, 0.13 g/g/h, 0.14 g/g/h or 0.15 g/g/h, most preferably $q_S$ is about 0.12 g/g/h.

7. The method of item 3, wherein $q_S$ is controlled and ramped down during at least 50% time the production phase of said POI.

8. The method according to item 6, wherein $q_S$ is decreases from 0.15 to 0.05 g/g/h, preferably from 0.15 to equal to or less than 0.12 g/g/h, from 0.15 to 0.10 g/g/h, from 0.15 to 0.07 g/g/h, from 0.15 to 0.05 g/g/h, from 0.12 to 0.1 g/g/h, from 0.12 to 0.07 g/g/h, from 0.12 to 0.05 g/g/h, from 0.1 to 0.07 g/g/h, from 0.1 to 0.05 g/g/h, or from 0.1 to 0.03 g/g/h.

9. The method of any one of the preceding items, wherein $q_S$ is controlled by adjusting the feed rate.

10. The method of any one of the preceding items, wherein $q_S$ is controlled by a feedback controlled specific substrate uptake rate.

11. The method of any one of the preceding items, wherein said feeding strategy is physiologically controlled by quantifying the biomass.

12. The method of items 11, wherein the biomass is determined by biomass estimation/–measurement.

13. The method of items 12, wherein the biomass is determined by real time biomass estimation/–measurement 14. The method of item 13, wherein real time biomass measurement is performed using a soft sensor or a hard sensor.

15. The method of any one of the preceding items, wherein the substrate is glucose or glycerol.

16. The method of any one of the preceding items, wherein the cells are selected from the group consisting of a eukaryotic cell or prokaryotic cell.

17. The method of item 16, wherein the eukaryotic cell is selected from the group consisting of mammalian, insect, yeast, filamentous fungi, and plant cell, preferably a yeast cell, most preferably *Pichia pastoris, Komagataella pastoris, K. phaffii,* or *K. pseudopastoris.*

18. The method of item 16, wherein the prokaryotic cell is selected from the group consisting of *E. coli, B. subtilis,* and *Pseudomonas.*

19. The method of item 18 wherein the prokaryotic cell is *E. coli.*

20. The method of item 16, wherein the majority of the POI is located in the cytoplasm, the periplasm or extracellularly.

21. The method of any one of the preceding items, wherein the POI is expressed using an expression system or expression cassette comprising a regulatable promoter operably linked to the nucleic acid encoding the POI.

22. The method of items 21, wherein the regulatable promoter is a inducible promoter or a depletion inducible promoter 23. The method of item 21 or 22, wherein the inducible promoter is a rhamnose promoter, a melibiose promoter, a mannose promoter, a arabinose promoter, a T5 promoter, a T7 promoter, a lac promoter, or an IPTG inducible promoter.

24. The method of item 23, wherein the rhamnose promoter is rhaBAD.

25. The method of any one of the preceding items, wherein the POI is a heterologous protein, preferably selected from therapeutic proteins, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI.

26. The method of item 25, wherein the therapeutic protein is an antigen binding molecule, preferably an immunoglobulin, more preferably an antibody or antibody fragment, most preferably a Fab or scFv antibody.

27. The method of any of the preceding items, wherein the prokaryotic cell is *E. coli* and the promoter is rhaBAD.

28. A method for producing a recombinant protein of interest (POI) comprising:
(a) culturing cells in a cell culture medium to express said POI by adding a feed comprising at least one substrate to said cell culture, and
(b) setting $q_S$ to be slightly above the maintenance rate of the cell culture; and
(c) isolating said POI from the cell culture.

The method of item 28, wherein $q_S$ is in the range of 0.03 to 0.15 g/g/h, preferably of 0.05 to 0.12 g/g/h, more preferably of 0.08 to 0.12 g/g/h, most preferably $q_S$ is about 0.12 g/g/h.

Examples

The examples which follow are set forth to aid in the understanding of the invention but are not intended to, and should not be construed to limit the scope of the invention in any way. The examples do not include detailed descriptions of conventional methods, e.g., cloning, transfection, and basic aspects of methods for protein expressing in microbial host cells. Such methods are well known to those of ordinary skill in the art.

Examples

Figure 1B:
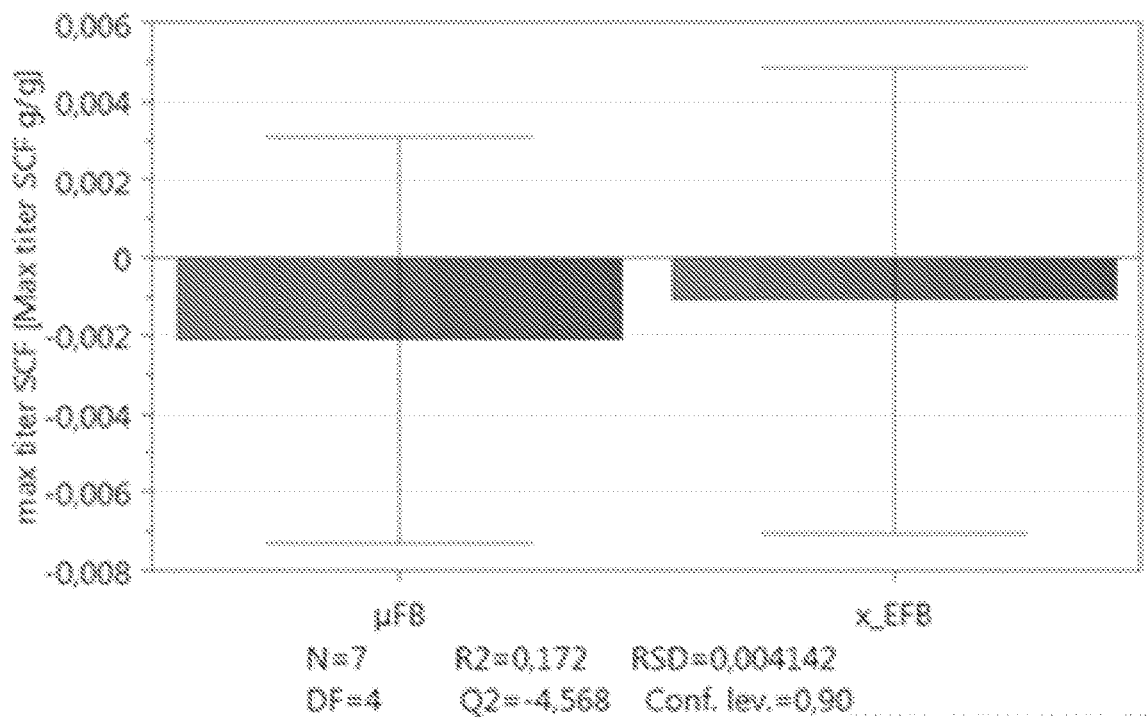
FIG. 1B Scaled and centered multi-linear regression model: x_EFB the biomass [g/L] at induction and μFB the pre-induction specific growth rate [1/h] were included as linear terms. The maximum specific titers served as response.

A two factor screening design (DoE) has been selected for the investigation of the impact of pre-induction specific growth rate and the biomass concentration at the point of induction. In order to account for differences in different biomass concentrations the volumetric constant feeding rate during induction was based on the same specific substrate uptake ($qs_{init}$ see Equation 3) and (FIGS. 1A and 1B).

To increase transferability the goal of the investigation is a physiological causative explanation of observed correlations of process parameters with maximum specific titers. On the basis of the data of the respective DoE the most promising physiological descriptor shall be identified by the help of a principal component analysis. Using an information mining approach physiology shall be linked with maximum specific titers to select the factors for subsequent investigation.

Hereby, physiology is described by single numeric values, corresponding to the average of a time dependent physiologic variables within a defined process phase—physiological descriptors.

Materials and Methods

A modified K12 *E. coli* strain was used as a model expression system. The strain features a rhamnose-inducible expression system (rhaBAD promoter; WO2006061174A2). The recombinant protein product was a Fab antibody. Since the strain is unable to utilize rhamnose as a carbon source, a one-time addition of inducer was sufficient.

For fermentation a predefined media was used (Wilms, Hauck et al. 2001).

Fed-batch experiments were conducted in a DASGIP multi-bioreactor system consisting of four glass bioreactors with a working volume of 2 L each (Eppendorf; Hamburg, Germany). The reactors are equipped with baffles and three disk impellers stirrers. The DASGIP control software v4.5 revision 230 was used to control the process parameters: pH (Hamilton, Reno, USA) and $pO_2$ (Mettler Toledo; Greifensee, Switzerland; module DASGIP PH4PO4), temperature and stirrer speed (module DASGIP TC4SC4) and aeration (module DASGIP MX4/4). The pH control was facilitated by 12.5% $NH_4OH$ base addition by the pump module DASGIP MP8. Feed was added using the same pump module. The reactors were sterilized at 121° C. for 20 min. $CO_2$, $O_2$ concentrations in the off-gas were quantified by a gas analyzer (module DASGIP GA4) using the non-dispersive infrared and zircon dioxide detection principle, respectively. The gas flow was controlled by the gas mixing module DASGIP GA4.

The pre-culture was inoculated in shake flasks from frozen stocks (100 mL in 1 L flasks). After approx. 17 h at 30° C. and 200 rpm, a volume equivalent of pre-culture of 2.5% of the batch volume was used to inoculate the batch media. After inoculation of the batch medium (20 g/L C-source), the C-source in the batch medium was consumed within 12 h. The pre-induction feeding strategy was based on an exponential feed forward profile according to Equation 1 and Equation 2. After the fed-batch, the culture was induced with rhamnose. The induction feed rate was calculated according to Equation 3 (Wechselberger et al., 2012) at the end of pre-induction the volumetric feed rate was left constant throughout induction phase. Dissolved oxygen levels ($DO_2$) were controlled over 25% (100% were set before inoculation at 35° C., 1 bar) by supplementing pure oxygen to the air. The pH was kept constant at 7 by adding 12.5% $NH_4OH$, which also served as nitrogen source. Temperature was set to 35° C. for the whole process.

$$F_{(t)} = F_0 * e^{(\mu * t)} \qquad \text{Equation 6}$$

$$F_0 = (x_0 * V_0 * \mu)/(c_{feed} * Y_{xs}) \qquad \text{Equation 7}$$

$$F_{ind} = (X_{EFB} * V_{EFB} * qs_{init})/(c_{feed}) \qquad \text{Equation 8}$$

Biomass dry cell weight concentrations were gravimetrically quantified after drying for 72 h at 105° C. The initial biomass concentration, which was required for the calculation of $F_0$ (Equation 7) was measured by photometric principle (OD 600 nm). Samples were diluted to the linear range of OD measurement <0.8 and consequently converted to a biomass concentration by the use of an established linear regression.

Offline samples were centrifuged (4300 rcf, 10 min) and pellets were washed with distilled water and then stored at −20° C. Frozen pellets were re-suspended in 100 mM Tris, 10 mM Na-EDTA, pH 7.4 to a final volume of 20 mL and homogenized at 1400±100 bar for 6 passages (Avestin EmulsiFlex, Ottawa, Canada).

The product quantity was measured by an industrial protein G affinity chromatography method using a pH gradient. Since only correctly folded product is bound the measurement of product quantity is also regarded as a measure of product quality.

Calculation of metabolic rates and yield coefficients was conducted with Matlab 2012 b (Mathworks, Natick, Mass., USA) Software was used for the calculation of specific rates and yield coefficients, as described in Wechselberger et al. (2012; Equations 8 and 9).

Since common DoE evaluation is based on the set points of the respective factors it does not take usual process deviation into account potentially masking effects triggered by potential set point deviations. To ensure the most realistic response to factor correlation, we used the actual met process variable as input instead of its mere set point.

Variables were tested for co-linearity with Datalab Version 3.5 (distributed by Epina http://datalab.epina.at/) multi-linear regression models were fitted and analyzed via the statistics software MODDE (Umetrics, Umeå, Sweden).

Results

To elucidate the impact of the pre-induction specific growth rate and the biomass concentration on productivity in induction phase, seven fermentation runs were conducted following a design of experiment (FIG. 1A). A screening design was selected whereby a range of pre-induction specific growth rate of 0.08-0.16 [1/h] and a range of biomass at induction of 20.7-44.6 [g/L] was investigated. In order to avoid an impact of the induction phase volumetric constant feeding profile was calculated and based on the same $qs_{init}$, calculated based on Equation 8, in all experiments (0.22+/−0.027 [g/g/h]).

To assess the H0 hypothesis: "pre-induction phase is independent of induction phase phase" statistical tests were performed.

According to statistical analysis (FIG. 1B), neither the specific growth rate ($\mu$) in pre-induction phase ($\mu$FB) nor the biomass (BM) at induction (x_EFB?) were found to significantly impact maximum specific titers of Fab antibody (SCF) during induction phase. (p=0.685; $\alpha$=0.1). Consequently H0 of no interrelation of pre- and post-induction phase is accepted.

In accordance with the work of Wechselberger et al. (2012) no interrelation of pre- and induction phase was detected for this expression system.

To investigate a possible impact of pre-induction phase on the physiology in induction phase all on- and off-line data was processed into specific rates and yield coefficients as outlined above.

Figure 2:
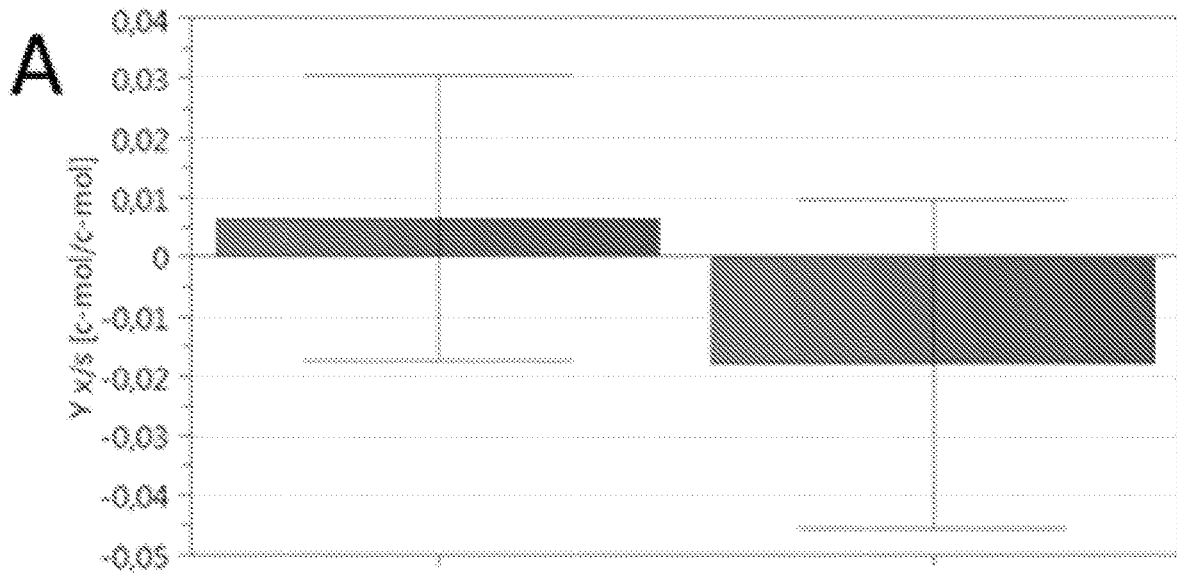
FIGS. 2A and 2B scaled and centered multi-linear regression model.
FIG. 2C: Principal component analysis with scaled and centered values.
Figure 2:
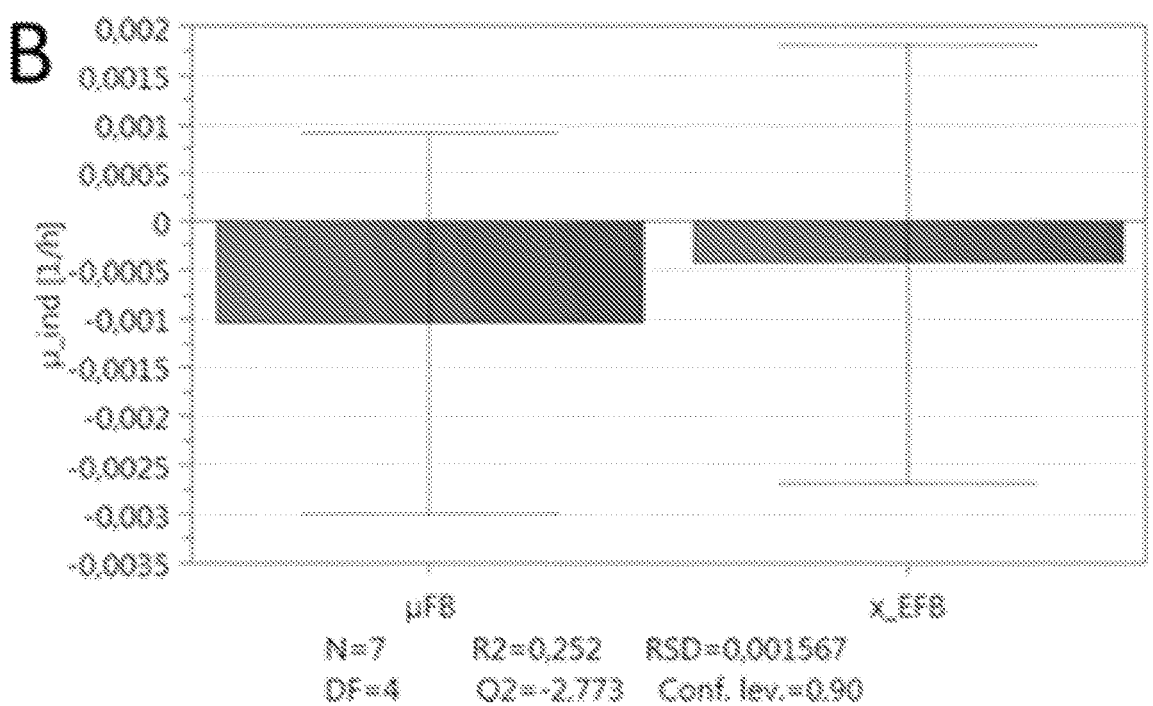
Figure 2:
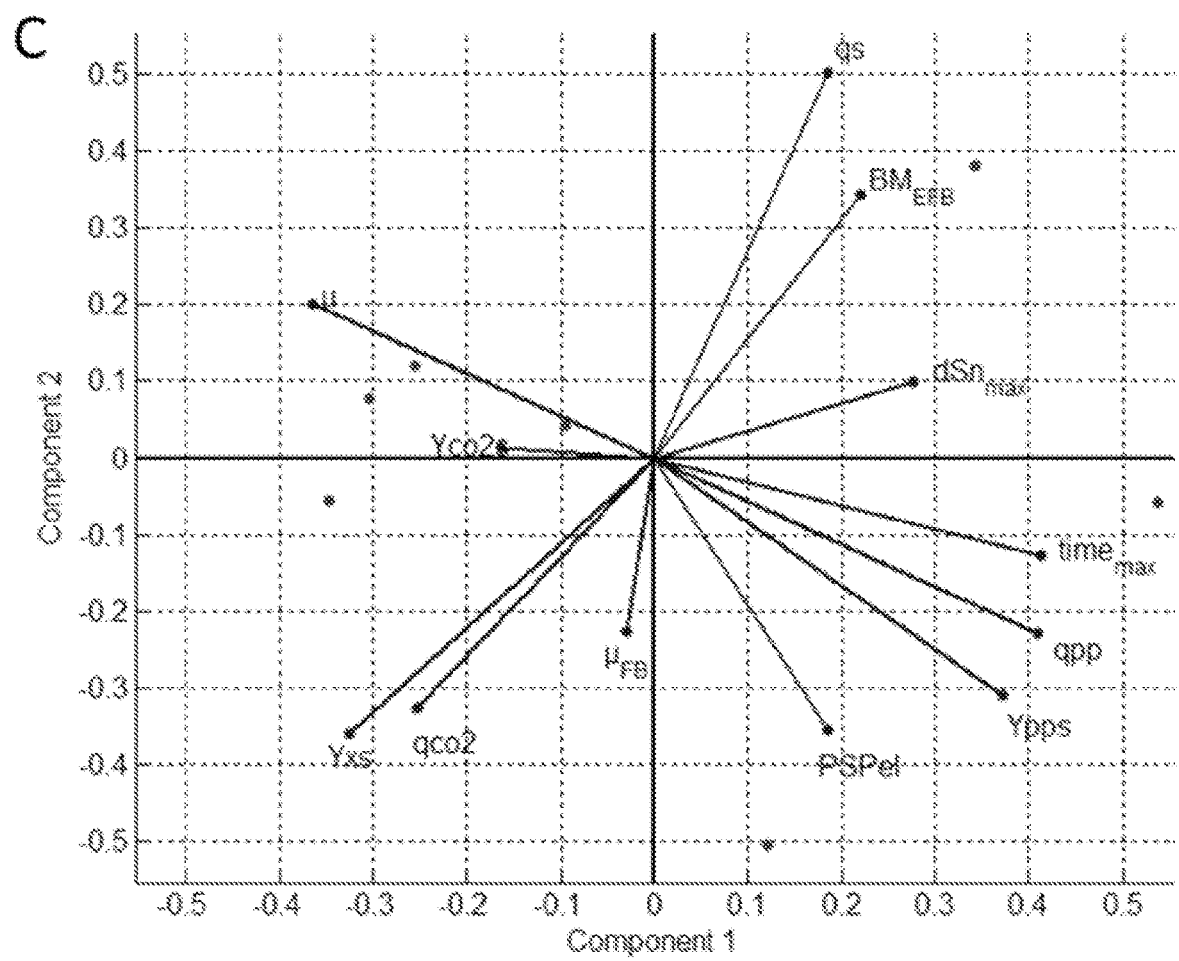
Figure 5:
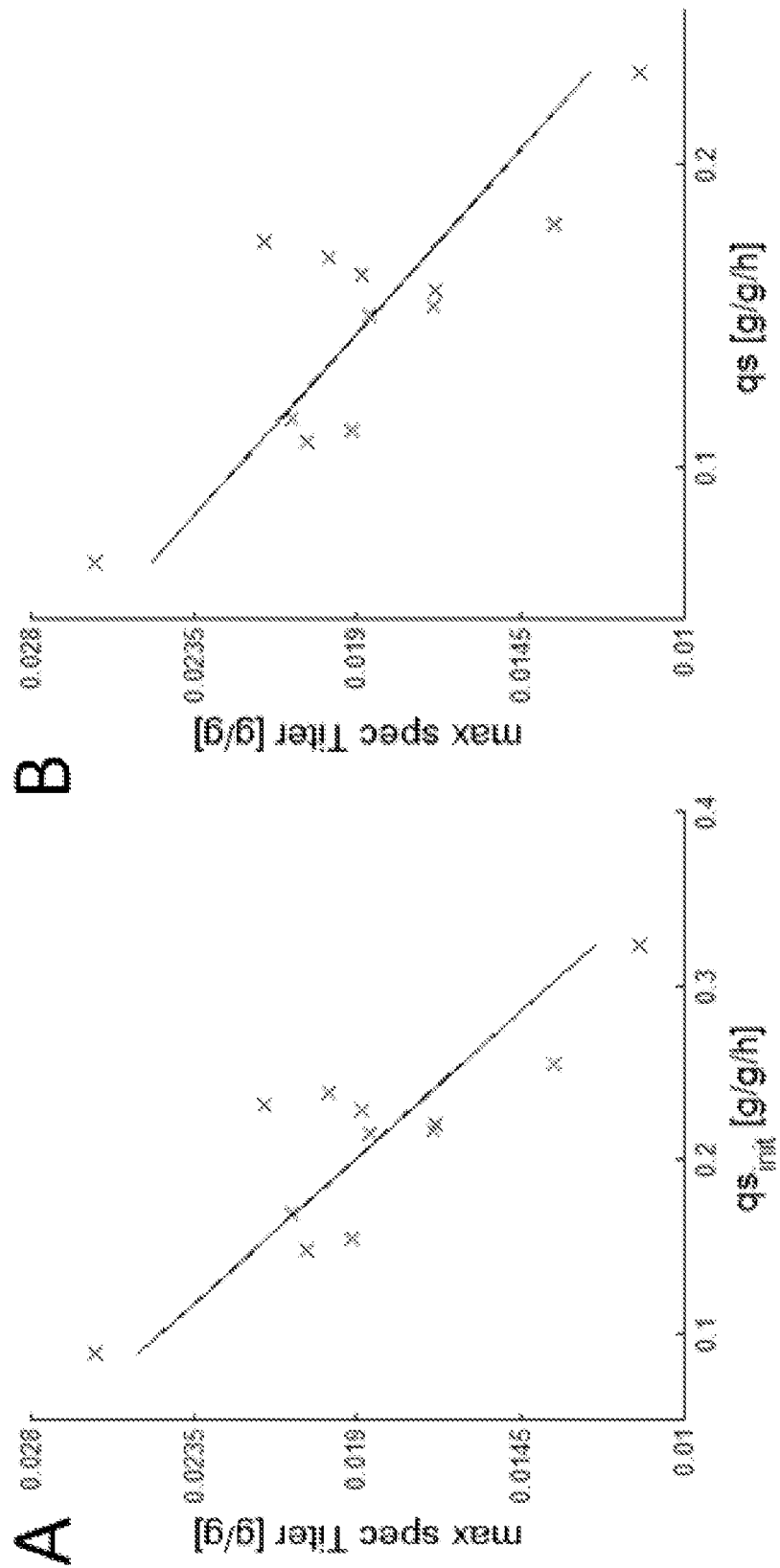
FIG. 5 shows the resulting variance in maximum specific titers [g/g]
Figure 5:
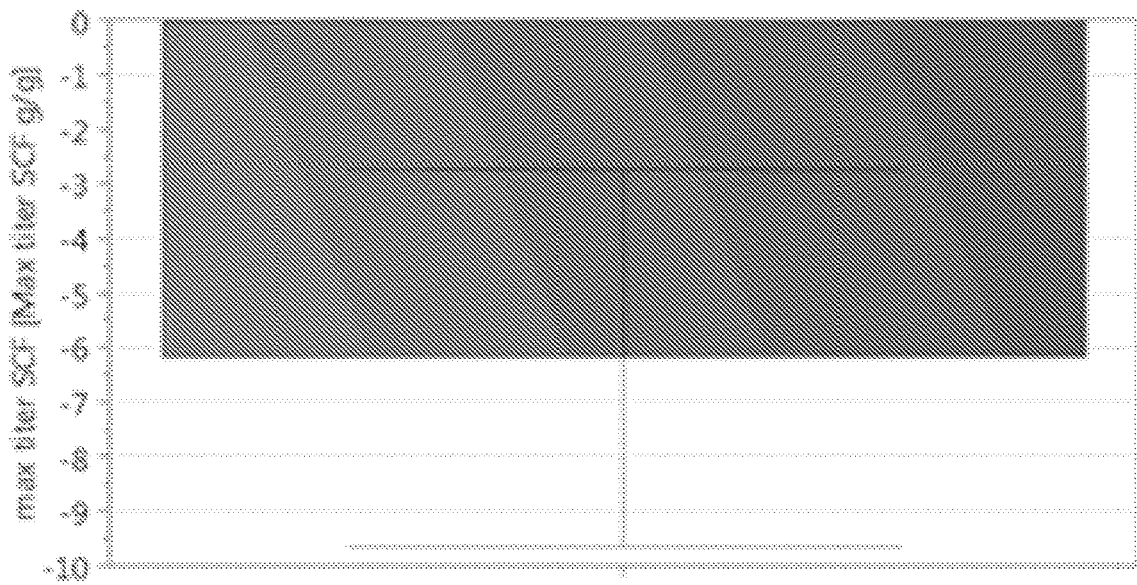
Figure 5:
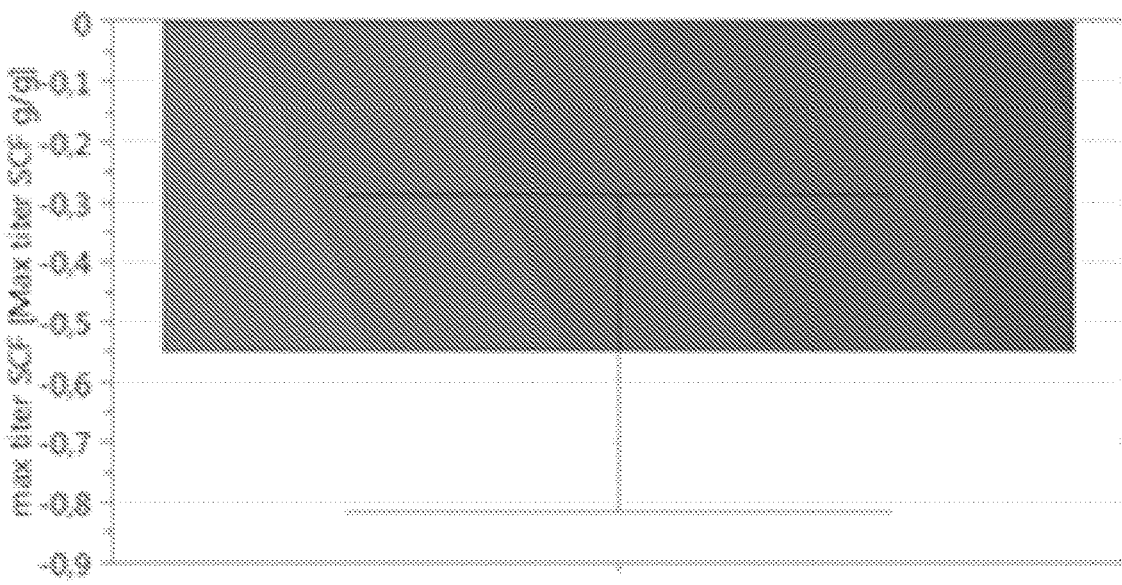

The physiological descriptor of the mean specific growth rate in induction phase is used as a response of the two factors: pre-induction specific growth rate ($\mu$FB) and biomass concentration at the end of pre-induction (x_EFB) (FIG. 2A). Further denying the hypothesized interrelation of pre- and induction phase is the finding that the two main physiological descriptors namely the biomass yield coefficient ($Y_{X/S}$) (FIG. 2A) and the specific growth rate in induction phase ($\mu$ind) (FIG. 2B) do not correlate with the specific growth rate during pre-induction ($\mu$FB) and biomass concentration at the end of pre-induction phase (x_EFB). Besides induction phase productivity also induction phase physiologic descriptors were not significantly affected by pre-induction specific growth rate and biomass concentration. However, although the original design of experiment (DoE) factors is not significant (FIGS. 1A and 1B), variance in the maximum specific product titer variance was observed (FIG. 5A). This raises the question of a physiologic explanation.

Owned to the observed variance in the specific titer (0.0137+/−0.0255 [g/g] of Fab antibody (see FIG. 5A) a comprehensive bioprocess analysis is of utmost importance in order to identify the physiological cause. Therefore, all variance contained within the set of selected process parameters and physiological descriptors were analyzed using a principal component analysis (FIG. 2C).

FIG. 2C shows a principal component analysis with scaled and centered values: $\mu$ specific growth rate [1/h]; $\mu_{FB}$ specific growth rate during pre-induction [1/h]; $BM_{EFB}$ biomass concentration at the end of pre-induction phase [g/L]; $q_S$ specific substrate uptake rate [g/g/h]; PSPel maximum specific titer [g/g]; $time_{max}$ time until maximum specific titer [h]; $dSn_{max}$ amount of normalized substrate metabolized until maximum specific titer [g/g]; $q_{CO2}$ specific carbon dioxide excretion rate [g/g/h]; qpp specific productivity [g/g/h]; $Y_{CO2}s$ carbon dioxide yield per substrate [g/g]; Ypps product yield per substrate [g/g]; $Y_{X/S}$ biomass yield [g/g].

The PCA is suggesting a negative correlation of the specific growth rate $\mu$ and the maximum specific product titer (FIG. 2C). Whereas the impact of the two pre-induction descriptors biomass at the end of pre-induction phase $BM_{EFB}$ and pre-induction specific growth rate µFB on the maximum specific titer appears to be marginal. The analysis of physiological parameters strongly points towards the specific growth rate as cause for alterations in the maximum specific titer PSPel.

Aiming for further bioprocess development the information mining approach facilitates factor selection based on empirical data rather than on theoretical risk assessment. As a consequence the modulation µ is indicated within the subsequent DoE. But targeting a highly transferable and simplistic bioprocess limits the feeding strategy to a constant volumetric flow rate. Calculating the appropriate feeding flow rate requires knowledge of the respective biomass concentration at the point of induction. By using µ as basis for calculation bears a greater risk of error propagation of the biomass estimation, then basing the calculation on $qs_{init}$. The linear DoE (n=5) included two levels of $qs_{init}$ (0.088-0.323 [g/g/h]) and featured two center points.

Figure 3:
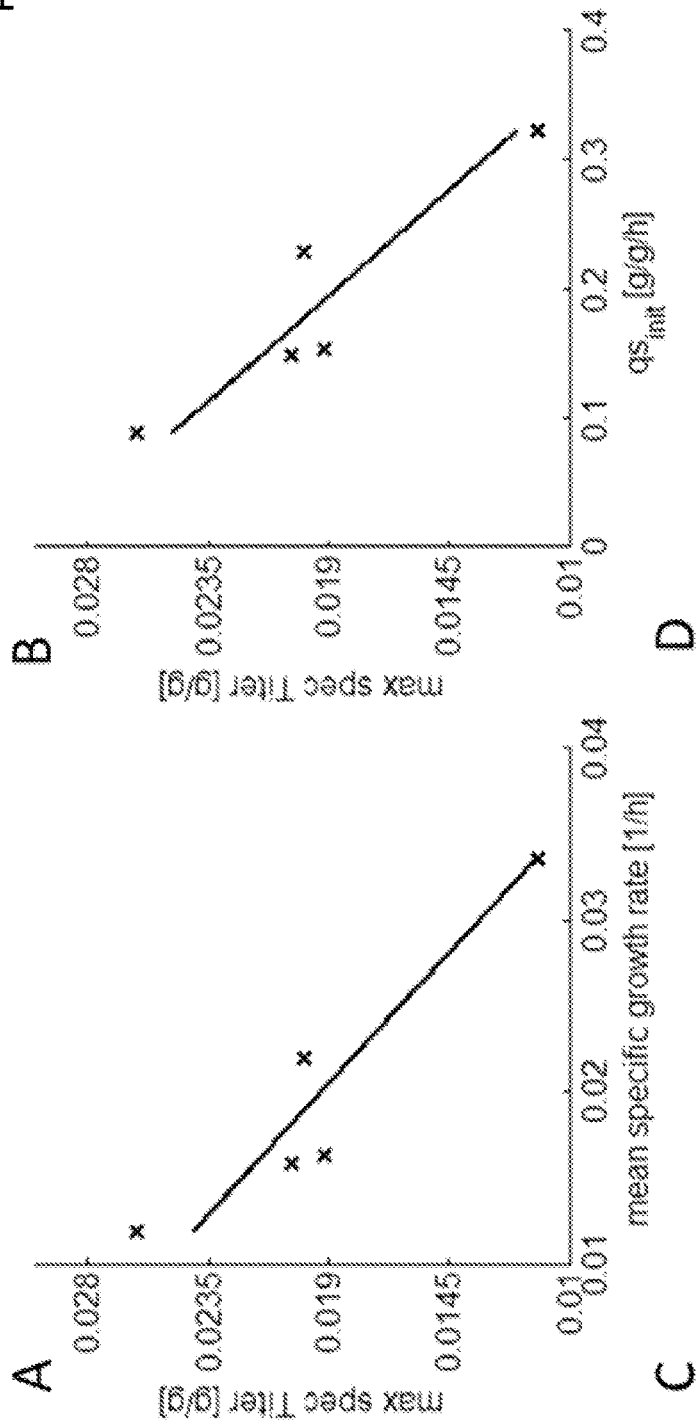
FIG. 3A: Correlation of the maximum specific titer [g/g] and mean induction phase specific growth rate [1/h].
FIG. 3B: Correlation of the maximum specific titer [g/g] and $q_{S_{init}}$ at the end of pre-induction calculated specific substrate uptake rate [g/g/h]
FIG. 3C: Statistical regression analysis: the specific growth rate [1/h] was correlated with the maximum specific titer as response.
FIG. 3D: Statistical regression analysis: $q_{S_{init}}$ at the end of pre-induction phase calculated specific substrate uptake rate [g/g/h] was correlated with the maximum specific titer as response.
Figure 3:

As illustrated in FIG. 3B, a negative correlation of maximal specific titers $qs_{init}$ levels was observed. $qs_{init}$ is a significant factor for maximal specific titers with a confidence level of 0.95 R 2 0.863/Q2 0.652. The highest specific titers were found at the lowest achieved $qs_{init}$.

Figure 4A:
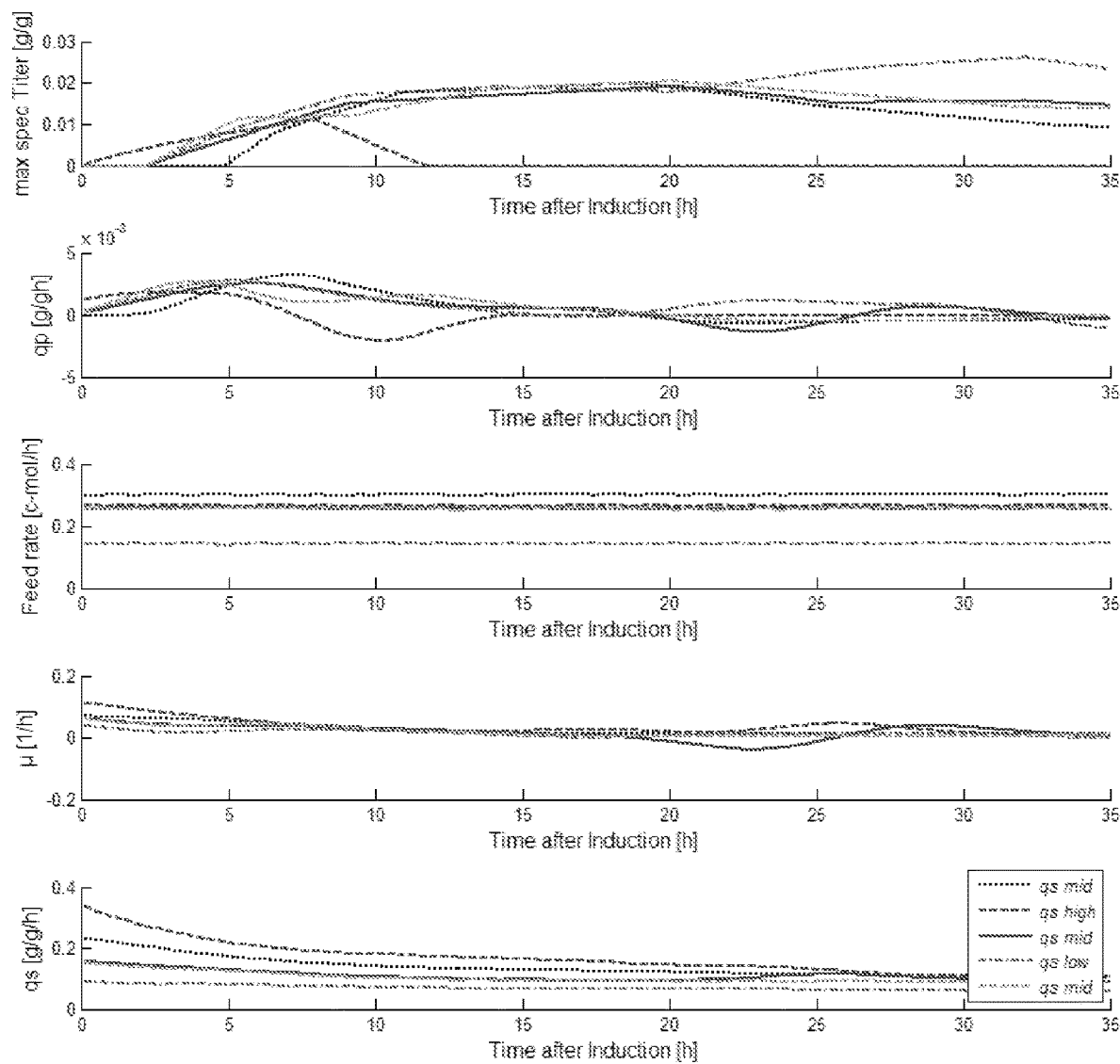
FIG. 4A: Trajectories of specific titer, specific productivity qp [g/g/h], feed rate [g/h], specific growth rate μ [1/h] and specific substrate uptake rate $q_S$ [g/g/h] plotted against time after induction [h].
Figure 4B:
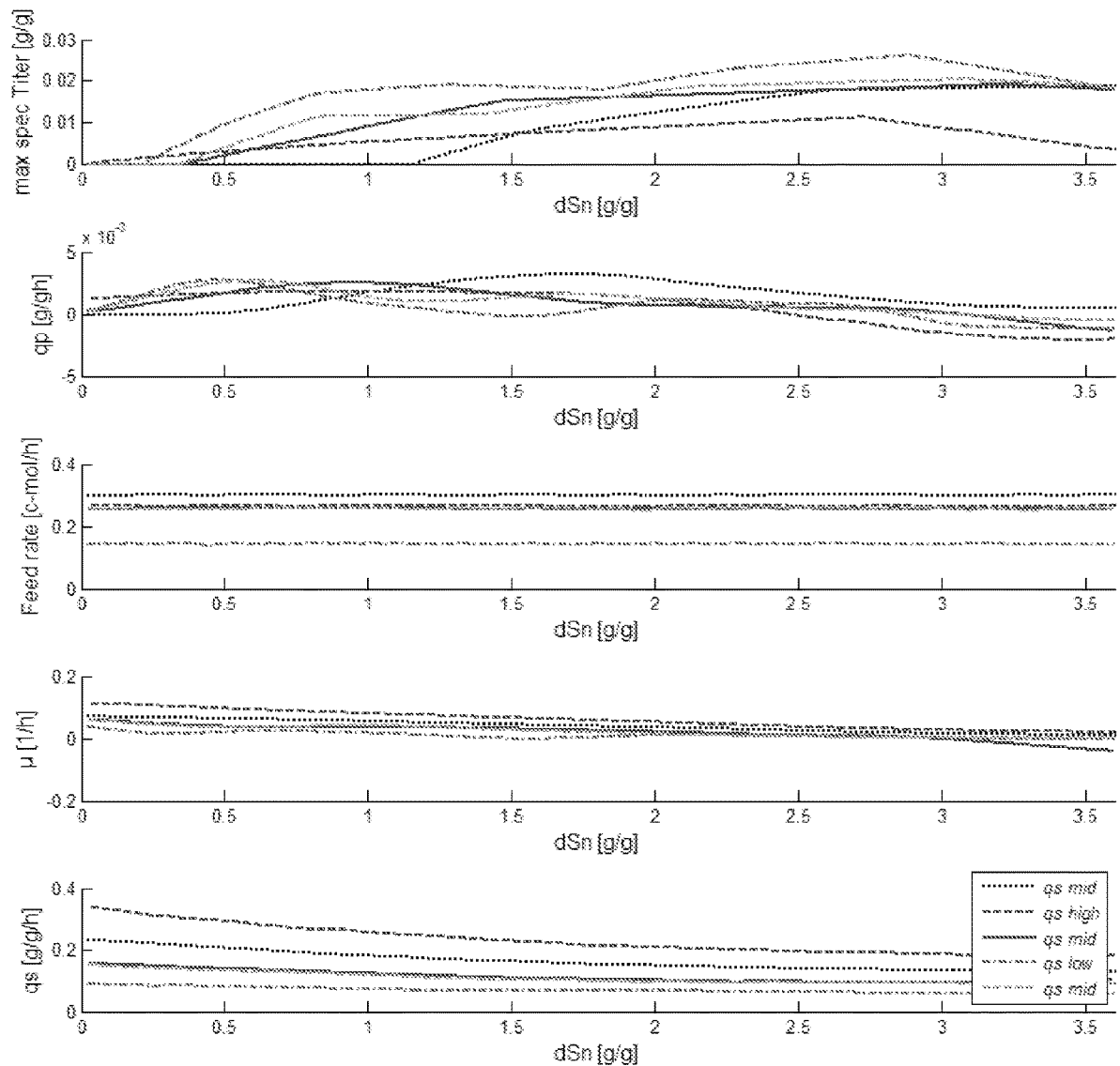
FIG. 4B: Trajectories of specific titer, specific productivity qp [g/g/h], feed rate [g/h], specific growth rate μ [1/h] and specific substrate uptake rate $q_S$ [g/g/h] plotted against dSn cumulated fed substrate normalized on the amount of biomass at induction [g/g].

In order to impact the specific growth rate, $qs_{init}$ was modulated by adjusting the feeding rate according to Equation 8. An investigation strategy based on feeding rate raises the question whether the substrate or time is the relevant dimension of age for *E. coli* Owned to the strong impact of the feeding rate differences in titers could be caused by a higher production rate or by a more efficient production of product. For this reason we substituted time on the x-axis with the cumulated amount of fed substrate (FIG. 4B). Normalization is necessary since different amounts of biomass at the end of pre-induction imply different feeding rates when calculated based on $qs_{init}$ (Equation 8). Consequently for the sake of transferability the amount fed substrate was normalized on the amount of biomass at the end of pre-induction phase yielding the variable dSn [g/g] Equation 9.

$$\Delta Sn(t) = (S_t - S_{EFB})/BM_{EFB} \quad \text{Equation 9}$$

Plotting the specific titer against time (FIG. 4A) visualizes the difference in the time point of reaching maximum specific titers. Maximum specific titers are reached much later in low $qs_{init}$ experiments than in high $qs_{init}$ experiments. Interestingly, plotting the maximum specific titers against dSn (FIG. 4B) aligns the product formation trajectories and the maximum specific titers can be found at similar dSn (3.1+/−0.336 g/g).

The calculation of physiologic descriptors as $q_s$ is conducted within a defined process phase. Within this contribution the window of calculation was based on the cumulative substrate uptake dSn. The process phase of interest corresponds to a dSn of 3.6 g/g for the calculation of every physiological descriptor. Consequently "$q_S$" is referring to the mean $q_S$ in induction phase calculated over a dSn of 3.6 g/g.

Figure 4C:
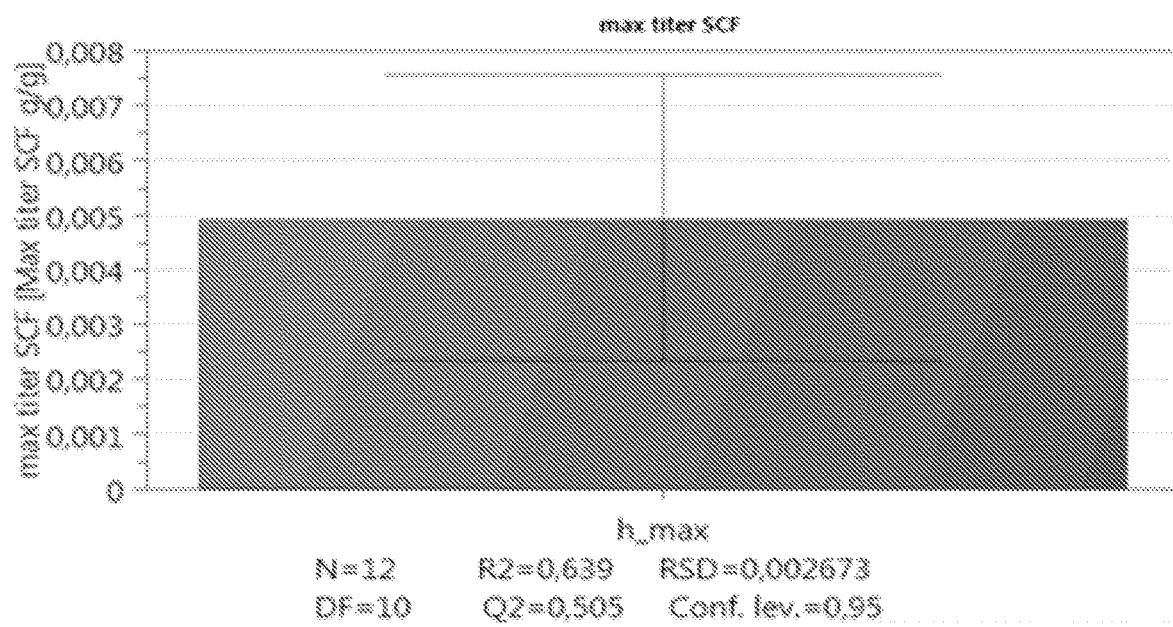
FIG. 4C: Statistical regression analysis: time until maximal specific titer h_max [h] was correlated with the maximum specific titer as response.
Figure 4D:
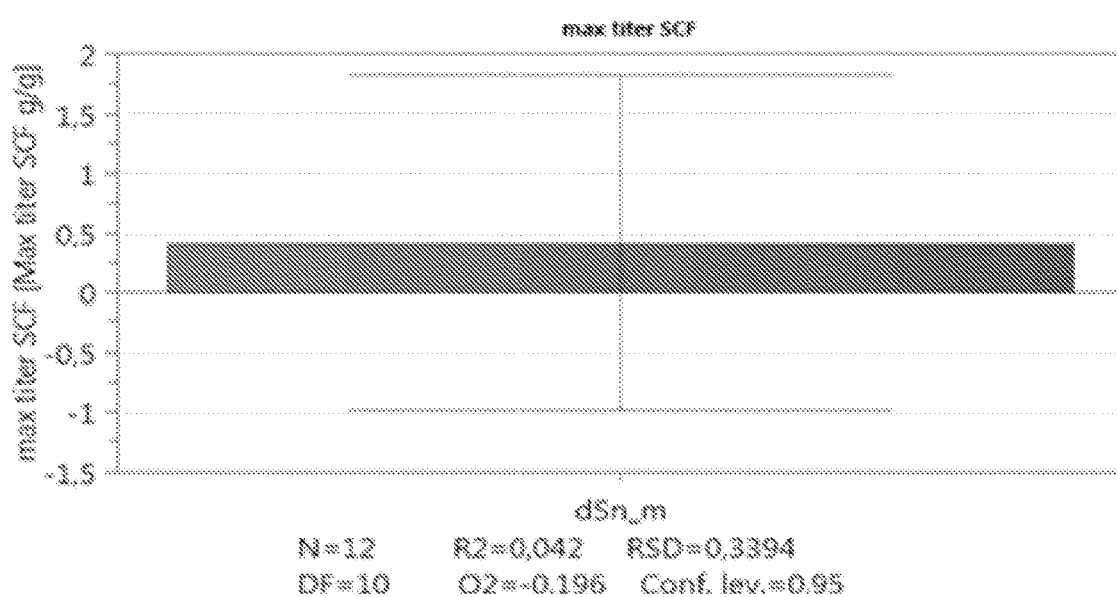
FIG. 4D: Statistical regression analysis: dSn cumulated fed substrate normalized on the amount of biomass at induction [g/g] was correlated with the maximum specific titer as response (Equation 4).

For statistical analysis the point of reaching the maximum specific titer of Fab antibody (SCF) in terms of time (FIG. 4C) and normalized fed substrate (dSn) (FIG. 4D) were compared. The analysis in form of a linear regression substantiates that the experiments differ significantly (R2=0.639; Q2=0.505) in terms of time point of reaching the max spec titers (FIG. 4C). Contrarily the amount of normalized fed feed (dSn) until the maximum specific titer was found to be insignificantly different (R2=0.042; Q2=0.196) (FIG. 4D). The max specific titers are reached at insignificantly different amounts of fed substrate dSn. Although the level of maximum specific titers is depending on $qs_{init}$ (FIG. 3B) the same amount of feed (dSn) is consumed until reaching significantly different maximum specific titers. This finding implicates that *E. coli* is using the same amount of fed substrate with different efficiency for product formation. Consequently insignificantly different amounts of substrate result in different amounts of product, featuring a significant difference in yield of product per substrate [g/g] (F=16/R2=0.62). These findings indicates that dSn is a powerful predictor for maximum specific titers and can be used to schedule (timing) the sampling effort within a bioprocess.

In terms information mining all conducted experiments is used to reassess previous findings based on all data (FIG. 5A/B). FIG. 5C-5E shall bring the difference of evaluating average and initial substrate uptake rates to the reader's attention.

Given the intention to optimize the bioprocess by modulating the most influential variable, the increase of variance (FIG. 5C qs_init variation vs. qs_init constant) was observed less pronounced in the maximum specific titer (FIG. 5E qs_init variation vs. qs_init constant). Due to the increase of biomass the amount of available substrate per cell and time declines ($q_S$) owned to the nature of a volumetric constant feeding profile (FIG. 4A). Initially the variation of $qs_{init}$ lead to strongly diverging amounts of available substrate per cell. But this difference in $q_S$ fades quickly as the trajectories of the real time qs converge fast. Although the initial difference in $qs_{init}$ is substantial, the difference in the physiological descriptor qs over the whole experiment is only minor (FIG. 5C/D). A process development approach based on $qs_{init}$ is strictly limited by the maximum substrate uptake rate, since substrate accumulation has to be avoided. To directly control the underlying physiological descriptor $q_S$ appears hereby far more promising, but requires advanced bioprocess control methods for real time biomass estimation. But the approach offers a much more direct modulation of maximum specific titers associated with a potentially higher range of variance induced in maximum specific titers

DISCUSSION

No significant interrelation of pre-induction phase and induction phase could be shown. By repeatedly testing the interrelation with two different expression systems the scope of the findings was extended to platform knowledge. The greater scope of the finding has the following consequences: it reduces the number of factors in any future experimental design within the platform and consequently speeds up bioprocess development (time to market).

Based on the platform specific prior knowledge that pre-induction phase has no significant effect on induction phase, the experiments investigating the impact of pre-induction phase can be omitted only constrained by the limits of the platform technology. The consequent feedback of found correlations into subsequent design of experiment increases the likelihood of selecting the most influential factors for further investigation within.

In an industrial context the fermentation is stopped and harvested once the maximum specific titer is reached. During bioprocess development following the PAT initiative sampling should facilitate a global process understanding, during bioprocess optimization sampling should be more focused on the process area where maximum specific titers are expected. Hence, it is important to analyze and predict when maximum specific titers occur in the induction phase.

The easy accessible but powerful predictor dSn will help to focus the invested effort in terms of sampling in regions of actual relevance. The increased time resolution in the area of highest specific titers will also facilitate a process optimization with high efficiency. Since the future of bioprocess development lies within small scale bioreactors the here presented simple method of prediction of highest titers becomes of additional interest. Where continuous time resolved sampling is limited by for example human resources and/or most and for all limited volume of small scale parallel bioreactors, sampling point selection is of utter importance and greatly eased by sampling according to dSn. A bioprocess development strategy based on $qs_{init}$ is been shown to be rewarding. Nevertheless a feeding strategy based in a constant volumetric feeding rate $qs_{init}$ is strongly limited by the physiological constraints that accumulation of metabolites has to be prevented. In this respect a dynamically adapted feed rate for constant $q_S$ grants more process technological freedom.

REFERENCES

Dabros, M., D. Dennewald, D. Currie, M. Lee, R. Todd, I. Marison and U. von Stockar (2009). "Cole-Cole, linear and multivariate modeling of capacitance data for on-line monitoring of biomass." Bioprocess and Biosystems Engineering 32(2): 161-173.

Dabros, M., M. Schuler and I. Marison (2010). "Simple control of specific growth rate in biotechnological fed-batch processes based on enhanced online measurements of biomass." Bioprocess and Biosystems Engineering 33(9): 1109-1118.

de Assis, A. J. and R. M. Filho (2000). "Soft sensors development for on-line bioreactor state estimation." Computers & Chemical Engineering 24(2-7): 1099-1103.

Dietzsch, C., O. Spadiut and C. Herwig (2011). "A dynamic method based on the specific substrate uptake rate to set up a feeding strategy for *Pichia pastoris*." Microb Cell Fact 10: 14.

Gnoth, S., M. Jenzsch, R. Simutis and A. Lübbert (2008). "Product formation kinetics in genetically modified *E. coli* bacteria: inclusion body formation." Bioprocess and Biosystems Engineering 31(1): 41-46.

Jenzsch, M., S. Gnoth, M. Beck, M. Kleinschmidt, R. Simutis and A. Lubbert (2006). "Open-loop control of the biomass concentration within the growth phase of recombinant protein production processes." J Biotechnol 127 (1): 84-94.

Jenzsch, M., R. Simutis, G. Eisbrenner, I. Stuckrath and A. Lubbert (2006). "Estimation of biomass concentrations in fermentation processes for recombinant protein production." Bioprocess Biosyst Eng 29(1): 19-27.

Jenzsch, M., R. Simutis and A. Luebbert (2006). "Generic model control of the specific growth rate in recombinant *Escherichia coli* cultivations." J Biotechnol 122(4): 483-493.

Jobe, A. M., C. Herwig, M. Surzyn, B. Walker, I. Marison and U. von Stockar (2003). "Generally applicable fed-batch culture concept based on the detection of metabolic state by on-line balancing." Biotechnol Bioeng 82(6): 627-639.

Passrinha, L. A., M. J. Bonifacio and J. A. Queiroz (2009). "Application of a fed-batch bioprocess for the heterologous production of hSCOMT in *Escherichia coli*." J Microbiol Biotechnol 19(9): 972-981.

Riesenberg, D., V. Schulz, W. A. Knorre, H. D. Pohl, D. Korz, E. A. Sanders, A. RoR and W. D. Deckwer (1991). "High cell density cultivation of *Escherichia coli* at controlled specific growth rate." Journal of Biotechnology 20(1): 17-27.

Sagmeister, P., P. Wechselberger, M. Jazini, A. Meitz, T. Langemann and C. Herwig (2013). "Soft sensor assisted dynamic bioprocess control: Efficient tools for bioprocess development." Chemical Engineering Science 96(0): 190-198.

Schaepe, S., A. Kuprijanov, R. Simutis and A. Lübbert (2014). "Avoiding overfeeding in high cell density fed-batch cultures of *E. coli* during the production of heterologous proteins." Journal of Biotechnology 192, Part A: 146-153.

Wechselberger, P., P. Sagmeister, H. Engelking, T. Schmidt, J. Wenger and C. Herwig (2012). "Efficient feeding profile optimization for recombinant protein production using physiological information." Bioprocess Biosyst Eng 35(9): 1637-1649.

Wechselberger, P., P. Sagmeister and C. Herwig (2013). "Real-time estimation of biomass and specific growth rate in physiologically variable recombinant fed-batch processes." Bioprocess Biosyst Eng 36(9): 1205-1218.

Wilms, B., A. Hauck, M. Reuss, C. Syldatk, R. Mattes, M. Siemann and J. Altenbuchner (2001). "High-cell-density fermentation for production of L-N-carbamoylase using an expression system based on the *Escherichia coli* rha-BAD promoter." Biotechnology and Bioengineering 73(2): 95-103.

The invention claimed is:

1. A method for producing a recombinant protein of interest (POI) comprising:
   (a) providing a regulatable promoter operably linked to a nucleic acid encoding the POI in prokaryotic cells or yeast cells;
   (b) culturing the cells in a cell culture medium that comprises at least one carbohydrate as the substrate carbon source;
   (c) setting the specific carbohydrate substrate uptake rate qs of the cells to be close to the maintenance rate of the cell culture during the expression phase of the POT, wherein said qs is in the range of 0.03 to 0.15 g/g/h;
   (d) expressing the POI in the prokaryotic cells or yeast cells; and
   (e) isolating the POI from the cell culture.

2. The method of claim 1, wherein the qs is controlled.

3. The method of claim 2, where in the qs is controlled to be constant, decreasing or increasing during at least 75% of the production phase of said POI.

4. The method of claim 2, wherein the qs is controlled at on a constant value (+/−15%) during at least 50% time of the production phase of said POI.

5. The method according to claim 4, wherein the qs is about 0.03 g/g/h, 0.04 g/g/h, 0.05 g/g/h, 0.06 g/g/h, 0.07 g/g/h, 0.08 g/g/h, 0.09 g/g/h, 0.1 g/g/h, 0.11 g/g/h, 0.12 g/g/h, 0.13 g/g/h, 0.14 g/g/h or 0.15 g/g/h.

6. The method of claim 2, wherein the qs is controlled and ramped down during at least 50% time the production phase of said POI.

7. The method according to claim 5, wherein the qs is decreases from 0.15 to 0.05 g/g/h.

8. The method of claim 1, wherein the qs is controlled by adjusting the feed rate or controlled by a feedback controlled specific carbohydrate uptake rate.

9. The method of claim 1, wherein said feeding strategy is physiologically controlled by quantifying the biomass.

10. The method of claim 9, wherein the biomass is determined by real time biomass estimation/-measurement.

11. The method of claim 1, wherein the carbohydrate is glucose or glycerol.

12. The method of claim 1, wherein the cells are selected from the group consisting of a prokaryotic cell.

13. The method of claim 12 wherein the cell is a prokaryotic cell, and the prokaryotic cell is *E. coli*.

14. The method of claim 1, wherein the regulatable promoter is an inducible promoter or a depletion inducible promoter.

15. The method of claim 1, wherein the regulatable promoter is an inducible promoter, and the inducible promoter is a rhamnose promoter, a melibiose promoter, a mannose promoter, a arabinose promoter, a T5 promoter, a T7 promoter, a lac promoter, or an IPTG inducible promoter.

16. The method of claim 1, wherein the POI is a heterologous protein.

17. A method for producing a recombinant protein of interest (POI) comprising:
  (a) culturing procaryotic or yeast cells in a cell culture medium to express said POI by adding a feed comprising at least one carbohydrate as the carbon source to said cell culture, wherein the POI is expressed using an expression system or expression cassette comprising a regulatable promoter operably linked to the nucleic acid encoding the POI,
  (b) setting the specific carbohydrate substrate uptake rate qs to be slightly above the maintenance rate of the cell culture, wherein said qs is in the range of 0.03 to 0.15 g/g/h; and
  (c) isolating said POI from the cell culture.

18. The method of claim 16, wherein the heterologous therapeutic protein is selected from enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI.

* * * * *